US008628918B2

(12) United States Patent  
Luo et al.

(10) Patent No.: US 8,628,918 B2  
(45) Date of Patent: *Jan. 14, 2014

(54) MULTIPLEX CAPTURE OF NUCLEIC ACIDS

(75) Inventors: Yuling Luo, San Ramon, CA (US); Wen Yang, Mountain View, CA (US)

(73) Assignee: Affymetrix, Inc., Santa Clara, CA (US)

( * ) Notice: Subject to any disclaimer, the term of this patent is extended or adjusted under 35 U.S.C. 154(b) by 406 days.

This patent is subject to a terminal disclaimer.

(21) Appl. No.: 11/431,092

(22) Filed: May 8, 2006

(65) Prior Publication Data

US 2006/0263769 A1    Nov. 23, 2006

Related U.S. Application Data

(60) Provisional application No. 60/679,500, filed on May 9, 2005.

(51) Int. Cl.
- *C12Q 1/68* (2006.01)
- *C12M 1/34* (2006.01)
- *C12P 19/34* (2006.01)
- *C07H 21/04* (2006.01)

(52) U.S. Cl.
USPC ....... 435/6.1; 435/91.1; 435/287.2; 536/23.1; 536/24.3

(58) Field of Classification Search
None
See application file for complete search history.

(56) References Cited

U.S. PATENT DOCUMENTS

| | | | |
|---|---|---|---|
| 4,868,105 A | 9/1989 | Urdea et al. | |
| 5,093,232 A | 3/1992 | Urdea et al. | |
| 5,122,599 A | 6/1992 | Barnett et al. | |
| 5,124,246 A | 6/1992 | Urdea et al. | |
| 5,185,244 A | 2/1993 | Wallace | |
| 5,198,357 A | 3/1993 | Holmovist et al. | |
| 5,334,499 A | 8/1994 | Burdick et al. | |
| 5,374,524 A | 12/1994 | Miller | |
| 5,393,672 A | 2/1995 | Ness et al. | |
| 5,543,305 A | 8/1996 | Cummins et al. | |
| 5,606,045 A | 2/1997 | Dandliker et al. | |
| 5,633,134 A | 5/1997 | Shuber | |
| 5,635,352 A | 6/1997 | Urdea et al. | |
| 5,681,697 A | 10/1997 | Urdea et al. | |
| 5,681,702 A | 10/1997 | Collins et al. | |
| 5,747,244 A | 5/1998 | Sheridan et al. | |
| 5,780,227 A | 7/1998 | Sheridan et al. | |
| 5,804,684 A | 9/1998 | Su | |
| 5,849,481 A | 12/1998 | Urdea et al. | |
| 5,888,778 A | 3/1999 | Shuber | |
| 5,945,515 A | 8/1999 | Chomczynski | |
| 6,007,994 A | 12/1999 | Ward et al. | |
| 6,221,589 B1 | 4/2001 | Lane et al. | |
| 6,268,147 B1 | 7/2001 | Beattie et al. | |
| 6,306,643 B1 | 10/2001 | Gentalen et al. | |
| 6,352,827 B1 | 3/2002 | Lin et al. | |
| 6,418,382 B2 * | 7/2002 | Rothberg et al. | 702/20 |
| 6,428,957 B1 | 8/2002 | Delenstarr | |
| 6,472,187 B1 | 10/2002 | Tonoike et al. | |
| 6,562,575 B1 | 5/2003 | Dahl | |
| 6,610,475 B1 | 8/2003 | Kacian et al. | |
| 6,670,464 B1 | 12/2003 | Shimkets et al. | |
| 6,673,914 B1 | 1/2004 | Hoon | |
| 6,852,490 B2 | 2/2005 | Gentalen et al. | |
| 2002/0034753 A1 * | 3/2002 | Yang et al. | 435/6 |
| 2002/0034754 A1 | 3/2002 | Reed et al. | |
| 2002/0106644 A1 | 8/2002 | Rosenow | |
| 2002/0172953 A1 * | 11/2002 | Mirkin et al. | 435/6 |
| 2002/0187470 A1 | 12/2002 | Casey et al. | |
| 2003/0165935 A1 | 9/2003 | Vann | |
| 2003/0211489 A1 * | 11/2003 | Shen et al. | 435/6 |
| 2004/0023248 A1 | 2/2004 | O'Malley | |
| 2004/0072231 A1 | 4/2004 | Mirkin et al. | |
| 2004/0076954 A1 | 4/2004 | Caldwell et al. | |
| 2004/0086930 A1 | 5/2004 | Tereba et al. | |
| 2004/0115686 A1 | 6/2004 | Dolginow et al. | |
| 2004/0248103 A1 | 12/2004 | Feaver et al. | |
| 2005/0009063 A1 | 1/2005 | Xia et al. | |
| 2005/0019842 A1 | 1/2005 | Prober et al. | |
| 2005/0170370 A1 | 8/2005 | Rabbani et al. | |
| 2005/0282220 A1 | 12/2005 | Prober et al. | |
| 2006/0172284 A1 | 8/2006 | Zheng et al. | |
| 2006/0263769 A1 | 11/2006 | Luo et al. | |
| 2006/0286583 A1 | 12/2006 | Luo et al. | |
| 2007/0015188 A1 | 1/2007 | Luo et al. | |
| 2007/0161015 A1 | 7/2007 | Zheng et al. | |
| 2007/0161020 A1 | 7/2007 | Luo et al. | |

(Continued)

FOREIGN PATENT DOCUMENTS

EP    1 428 892 A1    6/2004
WO    WO 94/00598 A1    1/1994

(Continued)

OTHER PUBLICATIONS

Bach et al. J. Microbiological Methods (1999) vol. 37, pp. 187-192.*
Dimitrov and Zuker (2004) "Prediction of hybridization and melting for double-stranded nucleic acids," *Biophysical Journal*, 87(1):215-226.
Baner et al. (1998) "Signal amplification of padlock probes by rolling circle replication," *Nucleic Acids Res.* 26(22):5073-5078.
Bushnell et al. (1999) "ProbeDesigner: for the design of probe sets for branched DNA (bDNA) signal amplification assays," *Bioinformatics*, 15(5):348-355.
Collins et al. (1997) "A branched DNA signal amplification assay for quantification of nucleic acid targets below 100 molecules/ml," *Nucleic Acids Research*, 25(15):2979-2984.
Collins et al. (1998) "Branched DNA (bDNA) technology for direct quantification of nucleic acids: design and performance," in *Gene Quantification*, F. Ferre, ed.

(Continued)

*Primary Examiner* — Sarae Bausch
(74) *Attorney, Agent, or Firm* — Quine Intellectual Property Law Group, P.C.; Monicia Elrod-Erickson

(57) ABSTRACT

Methods of capturing two or more nucleic acids simultaneously from a single sample are provided. Different nucleic acids are captured through cooperative hybridization events on different subsets of particles or at different selected positions on a spatially addressable solid support. Compositions, kits, and systems related to the methods are also described.

40 Claims, 5 Drawing Sheets

(56) References Cited

U.S. PATENT DOCUMENTS

| | | |
|---|---|---|
| 2008/0038725 A1 | 2/2008 | Luo et al. |
| 2008/0050746 A1 | 2/2008 | McMaster et al. |
| 2008/0176242 A1 | 7/2008 | McMaster et al. |
| 2008/0220979 A1 | 9/2008 | Wang et al. |
| 2009/0081688 A1 | 3/2009 | Luo et al. |
| 2009/0170060 A1 | 7/2009 | Kermekchiev et al. |

FOREIGN PATENT DOCUMENTS

| | | |
|---|---|---|
| WO | WO 01/94632 A2 | 12/2001 |
| WO | WO 2004/020654 A2 | 3/2004 |
| WO | WO 2006/124771 A2 | 11/2006 |

OTHER PUBLICATIONS

Flagella et al. (2006) "A multiplex branched DNA assay for parallel quantitative gene expression profiling," *Anal. Biochem.*, 352(1):50-60.

Fulton et al. (1997) "Advanced multiplexed analysis with the FlowMetrix system," *Clin Chem.*, 43:1749-1756.

Genospectra "Product Information Sheet for QuantiGene Plex Human Apoptosis Panel 1,"product literature, Oct. 14, 2004, pp. 1-2.

Genospectra "Product Information Sheet for QuantiGene Plex Human Apoptosis Panel 2,"product literature, Oct. 14, 2004, pp. 1-2.

Genospectra "Product Information Sheet for QuantiGene Plex Human Cytokine Panel 1,"product literature, Oct. 14, 2004, pp. 1-2.

Genospectra "QuantiGene Plex brochure," product literature, Oct. 14, 2004, pp. 1-4.

Genospectra "QuantiGene Plex panel brochure, " product literature, Oct. 14, 2004, p. 1.

Genospectra "QuantiGene® Plex Reagent System Instruction Manual," product literature, Oct. 14, 2004, pp. 1-26.

Gentalen & Chee. (1999) "A novel method for determining linkage between DNA sequences: hybridization to paired probe arrays," *Nucleic Acids Research*, 27(6):1485-1491.

Hatch et al. (1999) "Rolling circle amplification of DNA immobilized on solid surfaces and its application to multiplex mutation detection," *Genetic Anal.-Biomedical Engineering*, 15(2):35-40.

Iannone (2000) "Multiplexed single nucleotide polymorphism genotyping by oligonucleotide ligation and flow cytometry," *Cytometry*, 39(2):131-140.

Nallur et al. (2001) "Signal amplification by rolling circle amplification on DNA microarrays," *Nucleic Acids Res.*, 29(23):E118.

Wang et al. (1997) "Regulation of insulin preRNA splicing by glucose," *Proc. Nat. Acad. Sci. USA*, 94(9):4360-4365.

Wilber & Urdea (1998) "Quantification of HCV RNA in clinical specimens by branched DNA (bDNA) technology," *Methods in Molecular Medicine: Hepatitis C* 19:71-78.

Yang et al. (2001) "BADGE, Beads Array for the Detection of Gene Expression, a high-throughput diagnostic bioassay," *Genome Res.*, 11(11):1888-1898.

Zhang et al. (2005) "Small interfering RNA and gene expression analysis using a multiplex branched DNA assay without RNA purification," *Journal for Biomolecular Screening*, 10(6):549-556.

Van Cleve et al. (1998) "Direct quantification of HIV by flow cytometry using branched DNA signal amplification," *Molecular and Cellular Probes*, 12:243-247.

Al-Soud et al. (1998) "A sample preparation method which facilitates detection of bacteria in blood cultures by the polymerase chain reaction," *J. Microbiol. Meth.*, 32:217-224.

Application Note from Amersham Biosciences, "Whole genome amplification from crude blood lysates," 2003 (4 pages).

Application Note from Applied Biosystems, "Total RNA purification from whole blood," 2002 (6 pages).

Balnaves et al. (1991) "Direct PCR from CVS and blood lysates for detection of cystic fibrosis and Duchenne muscular dystrophy deletions," *Nucl. Acids. Res.*, 19(5):1155.

De Vries et al. (2001) "PCR on cell lysates obtained from whole blood circumvents DNA isolation," *Clin. Chem.* 47(9):1701-1702.

Higuchi (1989) "DNA from whole blood for PCR," *Amplifications*, 2:1-3 (One page from The Jackson Libaray, http://www.jax.org.imr.whole_blood.html).

Kern et al. (1996) "An enhanced-sensitivity branched-DNA assay for quantification of human immunodeficiency virus type 1 RNA in plasma," *J. Clin. Microbiol.*, 34(12):3196-3202.

Lewin & Stewart-Haynes (1992) "A simple method for DNA extraction from leukocytes for use in PCR," *BioTechniques*, 13(4):522-524.

Lo et al. (2000) "Fetal DNA in maternal plasma: biology and diagnostic applications," *Clinical Chemistry*, 46(12):1903-1906.

Malygin et al. (1996) "Hybridization of two oligodeoxynucleotides to both strands of an RNA hairpin structure increases the efficiency of RNA-DNA duplex formation," *FEBS Letters*, 392:114-116.

Mercier et al. (1990) "Direct PCR from whole blood, without DNA extraction," *Nucl. Acids. Res.*, 18(19):5908.

Narayanan (1992) "Overview of principles and current uses of DNA probes in clinical and laboratory medicine," *Ann. Clin. Lab. Sci.*, 22(6):353-376.

Nordvag et al. (1992) "Direct PCR of washed blood cells, " *BioTechniques*, 12(4):490-493.

Player et al. (2001) "Single-copy gene detection using branched DNA (bDNA) in-situ hybridization," *The Journal of Histochemistry and Cytochemistry*, 49(5):603-611.

Schweitzer & Kingsmore (2001) "Combining nucleic acid amplification and detection," *Curr. Op Biotechnol.*, 12(1):21-27.

Shah et al. (1994) "Novel, ultrasensitive, Q-beta, replicase-amplified hybridization assay for detection of *Chlamydia trachomatis*," *J. Clin. Microbiol.*, 32(11):2718-2724.

Shah et al. (1995) "Detection of *Mycobacterium tuberculosis* directly from spiked human sputum by Q-beta replicase-amplifiied assay," *J. Clin. Microbiol.*, 33(2):322-328.

Shah et al. (2003) "Ultra-sensitive and specific detections of porcine endogenous retrovirus (PERV) using a sequence-capture real-time PCR approach," *J. Virol.Meth.*, 109:209-216.

Stone et al. (1996) "Detection of rRNA from four respiratory pathogens using an automated Qβ replicase assay," *Mol. Cell. Probes*, 10:359-370.

Ugozzoli et al. (1992) "Detection of specific alleles by using allele-specific primer extension followed by capture on solid support," *GATA*, 9(4):107-112.

Zolg et al. (1988) "High salt lysates: a simple method to stores blood samples without refrigeration for subsequent use with DNA probes," *Am. J. Trop. Med. Hyg.*, 39(1):33-40.

Bortolin et al. (2004) "Analytical validation of the tag-it high-throughput microsphere-based universal array genotyping platform: application to the multiplex detection of a panel of thrombophilia-associated single-nucleotide polymorphisms," *Clin. Chem.*, 50(11):2028-2036.

Burris et al. (1999) "A novel method for analysis of nuclear receptor function at natural promoters: peroxisome proliferator-activated receptor γ agonist actions on aP2 gene expression detected using branched DNA messenger RNA quantitation," *Molecular Endocrinology*, 13(3):410-417.

Hartley and Klaassen (2000) "Detection of chemical-induced differential expression of rat hepatic cytochrome P450 mRNA transcripts using branched DNA signal amplification technology," *Drug Metabolism and Disposition*, 28(5):608-616.

Nolte (1998) "Branched DNA signal amplification for direct quantitation of nucleic acid sequences in clinical specimens," *Advances in Clinical Chemistry*, 33(1):201-235.

Shen et al. (1998) "Quantification of cytokine mRNA in peripheral blood mononuclear cells using branched DNA (bDNA) technology," *J. Immunol. Meth.*, 215(1-2):123-134.

Tsai et al. (2003) "Nucleic acid capture assay, a new method for direct quantitation of nucleic acids," *Nucleic Acids Research*, 31(6):e25.

Wilson et al. (2005) "A multiplexed PCR-coupled liquid bead array for the simultaneous detection of four biothreat agents," *Mol.Cell. Probes*, 19(2):137-144.

\* cited by examiner

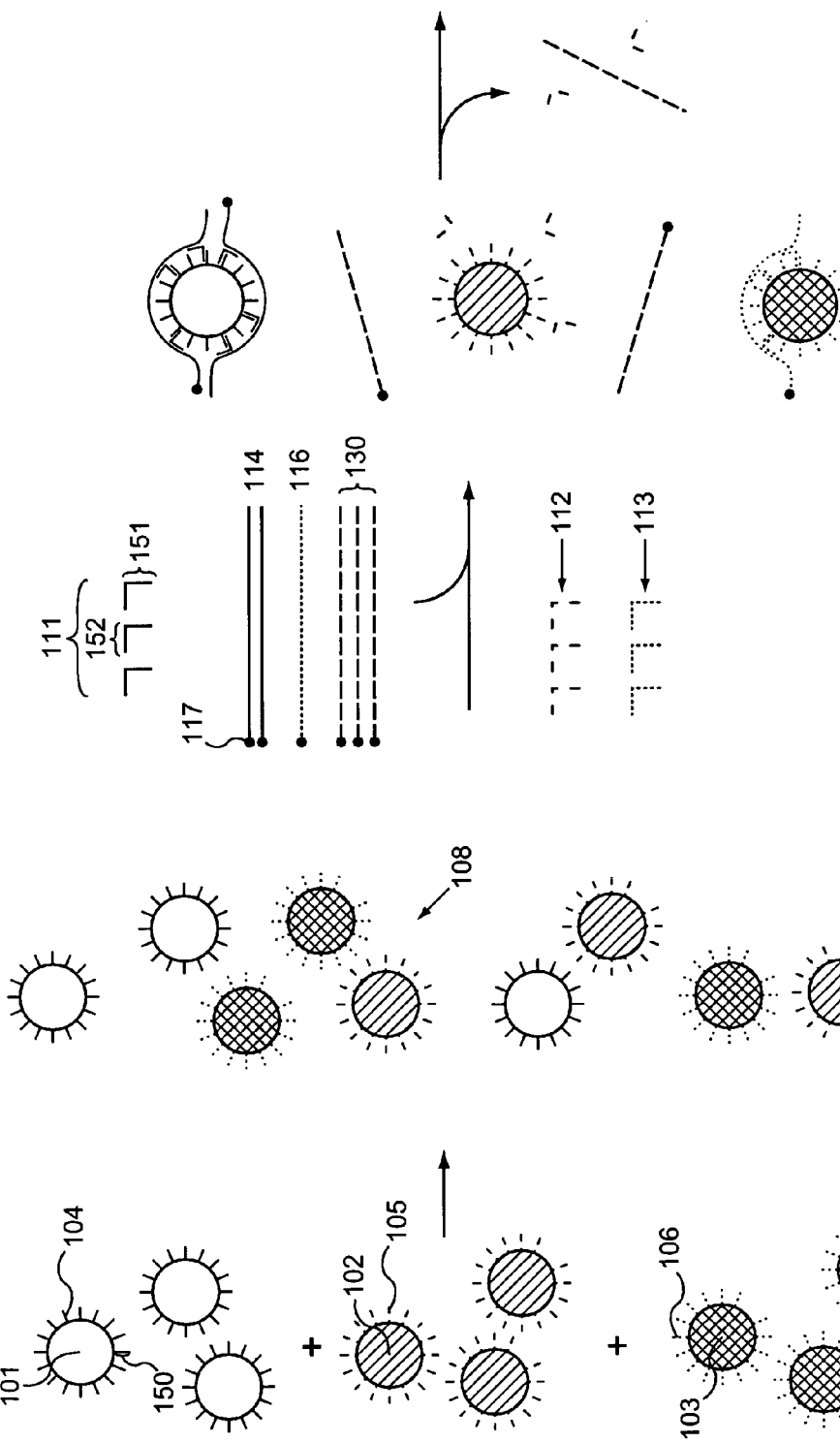

SEQUENCE LISTING

```
<160> NUMBER OF SEQ ID NOS: 70

<210> SEQ ID NO 1
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 1
agcagcaggc tctgcagctt tttttgtgca gtgttata                              38

<210> SEQ ID NO 2
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 2
gcgggtgcag agatgctgtt tttttgtgca gtgttata                              38

<210> SEQ ID NO 3
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 3
tacagctcca ggcgggtctt tttttgtgca gtgttata                              38

<210> SEQ ID NO 4
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 4
tgagcttggt gaggctgcct ttttttgtgc agtgttata                             39

<210> SEQ ID NO 5
<211> LENGTH: 39
<212> TYPE: DNA
<213> ORGANISM: Artificial
<220> FEATURE:
```

<223> OTHER INFORMATION: synthetic oligonucleotide probe

<400> SEQUENCE: 5
tgcttgtagt ggctggccat tttttttgtgc agtgttata                          39

<210> SEQ ID NO 6
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 6
ttttttttta taacactgca caa                                            23

<210> SEQ ID NO 7
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 7
tgacggtgcc atggaatttt ttttaaaact atacgtgct                           39

<210> SEQ ID NO 8
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 8
agcttcccgt tctcagcctt ttttaaaact atacgtgct                           39

<210> SEQ ID NO 9
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 9
tctcgctcct ggaagatggt tttttaaaac tatacgtgct                          40

<210> SEQ ID NO 10
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 10
gcaaatgagc cccagccttt ttaaaactat acgtgct                             37

<210> SEQ ID NO 11
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 11 cctttggct cccccctttt ttaaaactat acgtgct                              37

<210> SEQ ID NO 12

```
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 12
catggatgac cttggccagt ttttaaaact atacgtgct                                39

<210> SEQ ID NO 13
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 13
gctcagggat gaccttgcct ttttaaaact atacgtgct                                39

<210> SEQ ID NO 14
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 14 tttttttag cacgtatagt ttt                                                  23

<210> SEQ ID NO 15
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 15
cactctcctc tttccaattc ttcattttttt tttcacacac attaac                       46

<210> SEQ ID NO 16
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 16
ttggctctgc attatttttc tgttttttttt cacacacatt aac                          43

<210> SEQ ID NO 17
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 17
tctcgtttct ttttgttgct attgtttttt tcacacacat taac                          44

<210> SEQ ID NO 18
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 18
```

```
atgagttcat gtattgcttt gcgttttttt tcacacacat taac              44
```

<210> SEQ ID NO 19
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 19

```
ttccctgttt tagctgctgg ttttttttcac acacattaac                  40
```

<210> SEQ ID NO 20
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 20

```
atattcccca tataaataat gttaaatatt tttttttcac acacattaac         50
```

<210> SEQ ID NO 21
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 21

```
tttttttttgt taatgtgtgt gaa                                     23
```

<210> SEQ ID NO 22
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 22

```
agtgggtgca gctgttctca tttttccgtg cttttctaat                   40
```

<210> SEQ ID NO 23
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 23

```
ctcggagatc tcgaagcatg tttttccgt gcttttctaa t                  41
```

<210> SEQ ID NO 24
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 24

```
gctgatcctt catttgaaag aaattttcc gtgcttttct aat                43
```

<210> SEQ ID NO 25
<211> LENGTH: 41
<212> TYPE: DNA
<213> ORGANISM: Artificial
<220> FEATURE:

<223> OTHER INFORMATION: synthetic oligonucleotide probe

<400> SEQUENCE: 25
ctgggtcttg gttctcagct ttttttccgt gctttctaa t                 41

<210> SEQ ID NO 26
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 26
gcctcagcct gagggtcttt ttttccgtgc ttttctaat                   39

<210> SEQ ID NO 27
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 27
ccgattttgg agacctctaa tttattttc cgtgcttttc taat              44

<210> SEQ ID NO 28
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 28 tttttttat tagaaaagca cgg                                     23

<210> SEQ ID NO 29
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 29
gcagaggtcc aggtcctggt ttttaacgtg tattccatt                   39

<210> SEQ ID NO 30
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 30 tgaagcccett gctgtagtgg ttttttaacg tgtattccat t               41

<210> SEQ ID NO 31
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 31
cctggaaggt ctgtgggcat ttttaacgtg tattccatt                   39

<210> SEQ ID NO 32

```
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 32
aaagaaggtg ctcaggtcat tctttttaa cgtgtattcc att               43

<210> SEQ ID NO 33
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 33
ggagagcttt cagttcatat ggatttttaa cgtgtattcc att               43

<210> SEQ ID NO 34
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 34
ccatatcctg tccctggagg tttttttaacg tgtattccat t                 41

<210> SEQ ID NO 35
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 35
attcttttcc ttgaggccca tttttaacgt gtattccatt                    40

<210> SEQ ID NO 36
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 36 tttttttaa tggaatacac gtt                                       23

<210> SEQ ID NO 37
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 37
tgagtttggg attcttgtaa ttattaattt ttgaagttac cgttttc            47

<210> SEQ ID NO 38
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 38
```

```
tggccttctt gggcatgtat ttttgaagtt accgttttc                                39
```

<210> SEQ ID NO 39
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 39

```
ctccagaggt ttgagttctt cttcttttg aagttaccgt tttc                           44
```

<210> SEQ ID NO 40
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 40

```
tcagatccct ttagttccag aactttttg aagttaccgt tttc                           44
```

<210> SEQ ID NO 41
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 41

```
aataaataga aggcctgata tgttttattt ttgaagttac cgttttc                       47
```

<210> SEQ ID NO 42
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 42

```
ttttttttga aaacggtaac ttc                                                 23
```

<210> SEQ ID NO 43
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 43

```
gagcttctct ttcgttcccg tttttgggga acatagaaaa                               40
```

<210> SEQ ID NO 44
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 44

```
tgtggagaag gagttcatag ctgttttgg ggaacataga aaa                            43
```

<210> SEQ ID NO 45
<211> LENGTH: 37
<212> TYPE: DNA
<213> ORGANISM: Artificial
<220> FEATURE:

<223> OTHER INFORMATION: synthetic oligonucleotide probe

<400> SEQUENCE: 45
agccccaggg agaaggcttt ttggggaaca tagaaaa     37

<210> SEQ ID NO 46
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 46
tgtctccttt ctcagggctg atttttgggg aacatagaaa a     41

<210> SEQ ID NO 47
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 47
cctcattgaa tccagattgg aattttggg gaacatagaa aa     42

<210> SEQ ID NO 48
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 48
gaagagccct caggctggat ttttggggaa catagaaaa     39

<210> SEQ ID NO 49
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 49
tttttttttt ttctatgttc ccc     23

<210> SEQ ID NO 50
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 50
tgcacccagt tttccttggt tttttcaaa tgttagcct     39

<210> SEQ ID NO 51
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 51
ttttatgaat tctcagccct cttttttttt caaatgttag cct     43

<210> SEQ ID NO 52

```
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 52
cggatattct cttggccctt ttttttttcaa atgttagcct                              40

<210> SEQ ID NO 53
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 53
tgtggatcct ggctagcaga ttttttttcaa atgttagcct                              40

<210> SEQ ID NO 54
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 54
acccaattgt ttgtttgttt aatctttttt tcaaatgtta gcct                          44

<210> SEQ ID NO 55
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 55
ttttttttag gctaacattt gaa                                                 23

<210> SEQ ID NO 56
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 56
cgagaagatg atctgactgc ctgttttttct gagtcaaagc att                          43

<210> SEQ ID NO 57
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 57
gctgcccctc agcttgagtt tttctgagtc aaagcatt                                 38

<210> SEQ ID NO 58
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 58
```

```
gtctggtagg agacggcgat tttttctgag tcaaagcatt                              40
```

<210> SEQ ID NO 59
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 59

```
tcccagatag atgggctcat acttttctg agtcaaagca tt                           42
```

<210> SEQ ID NO 60
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 60

```
tcgggccgat tgatctcatt tttctgagtc aaagcatt                               38
```

<210> SEQ ID NO 61
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 61

```
cccccaattc tcttttgag cttttctga gtcaaagcat t                             41
```

<210> SEQ ID NO 62
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 62

```
tttttttaa tgctttgact cag                                                23
```

<210> SEQ ID NO 63
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 63

```
aaggctccaa tgcacccatt tttaggtttt ggattcat                               38
```

<210> SEQ ID NO 64
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 64

```
ctgccatggg tgcagccttt ttaggttttg gattcat                                37
```

<210> SEQ ID NO 65
<211> LENGTH: 39
<212> TYPE: DNA
<213> ORGANISM: Artificial
<220> FEATURE:

```
-continued

<223> OTHER INFORMATION: synthetic oligonucleotide probe

<400> SEQUENCE: 65
tggtgaggtt tgatccgcat ttttaggttt tggattcat                        39

<210> SEQ ID NO 66
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 66
atctctccta tgtgctggcc tttttaggt tttggattca t                      41

<210> SEQ ID NO 67
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 67
atctttcttt ggtctgcatt cactttttag gttttggatt cat                   43

<210> SEQ ID NO 68
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 68
ccctttccct ttcctcgaat ttttaggttt tggattcat                        39

<210> SEQ ID NO 69
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 69
ccaggactta taccgggatt tcttttagg ttttggattc at                     42

<210> SEQ ID NO 70
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 70
ttttttttat gaatccaaaa cct                                         23
```

MULTIPLEX CAPTURE OF NUCLEIC ACIDS

CROSS-REFERENCE TO RELATED APPLICATIONS

This application is a non-provisional utility patent application claiming priority to and benefit of the following prior provisional patent application: U.S. Ser. No. 60/679,500, filed May 9, 2005, entitled "MULTIPLEX CAPTURE OF NUCLEIC ACIDS" by Luo and Yang, which is incorporated herein by reference in its entirety for all purposes.

FIELD OF THE INVENTION

The present invention is in the field of nucleic acid hybridization. The invention includes methods for capturing two or more nucleic acids simultaneously from a single sample. The invention also includes compositions and kits related to the methods.

BACKGROUND OF THE INVENTION

A variety of techniques for detection of nucleic acids involve capture of the nucleic acids to a surface through hybridization of each nucleic acid to an oligonucleotide (or other nucleic acid) that is attached to the surface. For example, DNA microarray technology, which is widely used to analyze gene expression, relies on hybridization of DNA targets to preformed arrays of polynucleotides. See, e.g., Lockhart and Winzeler (2000) "Genomics, gene expression and DNA arrays" Nature 405:827-36, Gerhold et al. (2001) "Monitoring expression of genes involved in drug metabolism and toxicology using DNA microarrays" Physiol Genomics 5:161-70, Thomas et al. (2001) "Identification of toxicologically predictive gene sets using cDNA microarrays" Mol Pharmacol 60:1189-94, and Epstein and Butow (2000) "Microarray technology—enhanced versatility, persistent challenge" Curr Opin Biotechnol. 11:36-41.

A typical DNA microarray contains a large number of spots, with each spot containing a single oligonucleotide intended to hybridize to a particular nucleic acid target. For example, the GeneChip® microarray available from Affymetrix (Santa Clara, Calif.) includes thousands of spots, with each spot containing a different single 25 mer oligonucleotide. Multiple (e.g., about 20) oligonucleotides that are perfect matches for a particular target nucleic acid are typically provided, with each oligonucleotide being complementary to a different region of the target nucleic acid. Additional spots including mismatch oligonucleotides having a single nucleotide substitution in the middle of the oligonucleotide are also included in the array. Since binding to a single 25 mer may not result in specific capture of the target nucleic acid, statistical methods are used to compare the signals obtained from all the spots for a particular target nucleic acid (e.g., perfectly matched and mismatched oligonucleotides) to attempt to correct for cross-hybridization of other nucleic acids to those spots.

In another approach, longer probes are used to form the spots in the microarray. For example, instead of short oligonucleotides, longer oligonucleotides or cDNAs can be used to capture the target nucleic acids. Use of such longer probes can provide increased specificity, but it can also make discrimination of closely related sequences difficult.

Improved methods for capturing target nucleic acids to surfaces are thus desirable. Among other aspects, the present invention provides methods that overcome the above noted limitations and permit rapid, simple, and highly specific capture of multiple nucleic acids simultaneously. A complete understanding of the invention will be obtained upon review of the following.

SUMMARY OF THE INVENTION

In one aspect, the present invention provides methods of capturing two or more nucleic acids of interest. Different nucleic acids are captured through cooperative hybridization events on different subsets of particles or at different selected positions on a spatially addressable solid support. Compositions and kits related to the methods are also provided.

A first general class of embodiments provides methods of capturing two or more nucleic acids of interest. In the methods, a sample, a pooled population of particles, and two or more subsets of n target capture probes, wherein n is at least two, are provided. The sample comprises or is suspected of comprising the nucleic acids of interest. The pooled population of particles includes two or more subsets of particles. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. In one class of embodiments, a plurality of the particles in each subset are distinguishable from a plurality of the particles in every other subset. Each nucleic acid of interest can thus, by hybridizing to its corresponding subset of n target capture probes which are in turn hybridized to a corresponding support capture probe, be associated with an identifiable subset of the particles.

The sample, the pooled population of particles, and the subsets of n target capture probes are contacted, any nucleic acid of interest present in the sample is hybridized to its corresponding subset of n target capture probes, and the subset of n target capture probes is hybridized to its corresponding support capture probe. The hybridizing the nucleic acid of interest to the n target capture probes and the n target capture probes to the corresponding support capture probe captures the nucleic acid on the subset of particles with which the target capture probes are associated. The hybridizing the subset of n target capture probes to the corresponding support capture probe is performed at a hybridization temperature which is greater than a melting temperature $T_m$ of a complex between each individual target capture probe and its corresponding support capture probe.

The methods are useful for multiplex capture of nucleic acids, optionally highly multiplex capture. Thus, the two or more nucleic acids of interest (i.e., the nucleic acids to be captured) optionally comprise five or more, 10 or more, 20 or more, 30 or more, 40 or more, 50 or more, or even 100 or more nucleic acids of interest. A like number of subsets of particles and subsets of target capture probes are typically provided; thus, the two or more subsets of particles can comprise five or more, 10 or more, 20 or more, 30 or more, 40 or more, 50 or more, or even 100 or more subsets of particles, while the two or more subsets of n target capture probes can comprise five or more, 10 or more, 20 or more, 30 or more, 40 or more, 50 or more, or even 100 or more subsets of n target capture probes.

In one class of embodiments, the particles are microspheres. The microspheres of each subset can be distinguishable from those of the other subsets, e.g., on the basis of their fluorescent emission spectrum, their diameter, or a combination thereof.

As noted, each of the two or more subsets of target capture probes includes n target capture probes, where n is at least two. Preferably, n is at least three, and n can be at least four or at least five or more. Typically, but not necessarily, n is at most ten. The n target capture probes in a subset preferably hybridize to nonoverlapping polynucleotide sequences in the corresponding nucleic acid of interest.

Each target capture probe is capable of hybridizing to its corresponding support capture probe. The target capture probe typically includes a polynucleotide sequence U-1 that is complementary to a polynucleotide sequence U-2 in its corresponding support capture probe. In one aspect, U-1 and U-2 are 20 nucleotides or less in length. In one class of embodiments, U-1 and U-2 are between 9 and 17 nucleotides in length (inclusive), preferably between 12 and 15 nucleotides (inclusive).

As noted, the hybridizing the subset of n target capture probes to the corresponding support capture probe is performed at a hybridization temperature which is greater than a melting temperature $T_m$ of a complex between each individual target capture probe and its corresponding support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

In one class of embodiments, contacting the sample, the pooled population of particles, and the subsets of n target capture probes comprises combining the sample with the subsets of n target capture probes to form a mixture, and then combining the mixture with the pooled population of particles. In this class of embodiments, the target capture probes typically hybridize first to the corresponding nucleic acid of interest and then to the corresponding particle-associated support capture probe. The hybridizations can, however, occur simultaneously or even in the opposite order. Thus, in another exemplary class of embodiments, contacting the sample, the pooled population of particles, and the subsets of n target capture probes comprises combining the sample, the subsets of target capture probes, and the pooled population of particles.

The nucleic acids are optionally detected, amplified, isolated, and/or the like after capture. Thus, in one aspect, a plurality of the particles in each subset are distinguishable from a plurality of the particles in every other subset, and the methods include determining which subsets of particles have a nucleic acid of interest captured on the particles, thereby indicating which of the nucleic acids of interest were present in the sample. For example, in one class of embodiments, each of the nucleic acids of interest comprises a label (e.g., a fluorescent label), and determining which subsets of particles have a nucleic acid of interest captured on the particles comprises detecting a signal from the label. The methods can optionally be used to quantitate the amounts of the nucleic acids of interest present in the sample. For example, in one class of embodiments, an intensity of the signal from the label is measured, e.g., for each subset of particles, and correlated with a quantity of the corresponding nucleic acid of interest present. As another example, in one class of embodiments, determining which subsets of particles have a nucleic acid of interest captured on the particles comprises amplifying any nucleic acid of interest captured on the particles.

In one class of embodiments, one or more subsets of particles is isolated, whereby any nucleic acid of interest captured on the particles is isolated. The isolated nucleic acid can optionally be removed from the particles and/or subjected to further manipulation, if desired.

At any of various steps, materials not captured on the particles are optionally separated from the particles. For example, after the target capture probes, nucleic acids, and particle-bound support capture probes are hybridized, the particles are optionally washed to remove unbound nucleic acids and target capture probes.

The methods can be used to capture the nucleic acids of interest from essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen. As additional examples, the two or more nucleic acids of interest can comprise two or more mRNAs, bacterial and/or viral genomic RNAs and/or DNAs (double-stranded or single-stranded), plasmid or other extragenomic DNAs, or other nucleic acids derived from microorganisms (pathogenic or otherwise).

Due to cooperative hybridization of multiple target capture probes to a nucleic acid of interest, for example, even nucleic acids present at low concentration can be captured. Thus, in one class of embodiments, at least one of the nucleic acids of interest is present in the sample in a non-zero amount of 200 amol or less, 150 amol or less, 100 amol or less, 50 amol or less, 10 amol or less, 1 amol or less, or even 0.1 amol or less.

Capture of a particular nucleic acid is optionally quantitative. Thus, in one exemplary class of embodiments, the sample includes a first nucleic acid of interest, and at least 30%, at least 50%, at least 80%, at least 90%, at least 95%, or even at least 99% of a total amount of the first nucleic acid present in the sample is captured on a first subset of particles. Such quantitative capture can occur without capture of a significant amount of undesired nucleic acids, even those of very similar sequence to the nucleic acid of interest. Thus, in one class of embodiments, the sample comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the sample, is captured on a first subset of particles, while the second nucleic acid comprises 1% or less of a total amount of nucleic acid captured on the first subset of particles (e.g., 0.5% or less, 0.2% or less, or even 0.1% or less).

In one class of embodiments, the sample comprises a first nucleic acid of interest and a second nucleic acid, where the first nucleic acid is a first splice variant and the second nucleic acid is a second splice variant of the given mRNA. A first subset of n target capture probes is capable of hybridizing to the first splice variant, of which at most n−1 target capture probes are capable of hybridizing to the second splice variant. Preferably, hybridization of the n target capture probes to the first splice variant captures the first splice variant on a first subset of particles while hybridization of the at most n−1 target capture probes to the second splice variant does not capture the second splice variant on the first subset of particles.

Another general class of embodiments provides a composition that includes two or more subsets of particles and two or more subsets of n target capture probes, wherein n is at least two. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. When the nucleic acid of interest corresponding to a subset of n target capture probes is present in the composition and is hybridized to the subset of n target capture probes, which are hybridized to the corresponding support capture probe, the nucleic acid of interest is hybridized to the subset of n target capture probes at a hybridization temperature which is greater than a melting temperature $T_m$ of a complex between each individual target capture probe and the support capture probe. In one class of embodiments, a plurality of the particles in each subset are distinguishable from a plurality of the particles in every other subset.

The composition optionally includes a sample comprising or suspected of comprising at least one of the nucleic acids of interest. In one class of embodiments, the composition is maintained at the hybridization temperature and comprises one or more of the nucleic acids of interest; each nucleic acid of interest is hybridized to its corresponding subset of n target capture probes, the corresponding subset of n target capture probes being hybridized to its corresponding support capture probe.

Essentially all of the features noted for the methods above apply to these embodiments as well, as relevant; for example, with respect to number of target capture probes per subset, configuration of the target capture probes and/or support capture probes, number of nucleic acids of interest and of subsets of particles and target capture probes, type of particles, label configuration, source of the sample and/or nucleic acids, and/or the like.

A related general class of embodiments provides a composition comprising two or more subsets of particles, two or more subsets of n target capture probes, wherein n is at least two, and at least a first nucleic acid of interest. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. In this class of embodiments, the composition is maintained at a hybridization temperature, which hybridization temperature is greater than a melting temperature $T_m$ of a complex between each individual target capture probe and its corresponding support capture probe. The first nucleic acid of interest is hybridized to a first subset of n first target capture probes, which first target capture probes are hybridized to a first support capture probe. In one class of embodiments, a plurality of the particles in each subset are distinguishable from a plurality of the particles in every other subset.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, type of particles, label configuration, source of the sample and/or nucleic acids, and/or the like.

Yet another general class of embodiments provides a kit for capturing two or more nucleic acids of interest. The kit includes two or more subsets of particles and two or more subsets of n target capture probes, wherein n is at least two, packaged in one or more containers. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. When the nucleic acid of interest corresponding to a subset of n target capture probes is hybridized to the subset of n target capture probes, which are hybridized to the corresponding support capture probe, the nucleic acid of interest is hybridized to the subset of n target capture probes at a hybridization temperature which is greater than a melting temperature $T_m$ of a complex between each individual target capture probe and the support capture probe. The kit optionally also includes instructions for using the kit to capture and optionally detect the nucleic acids of interest, one or more buffered solutions (e.g., lysis buffer, diluent, hybridization buffer, and/or wash buffer), standards comprising one or more nucleic acids at known concentration, and/or the like. In one class of embodiments, a plurality of the particles in each subset are distinguishable from a plurality of the particles in every other subset.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, type of particles, label configuration, source of the sample and/or nucleic acids, and/or the like.

Another general class of embodiments includes methods of capturing two or more nucleic acids of interest. In the methods, a sample, a solid support, and two or more subsets of n target capture probes, wherein n is at least two, are provided. The sample comprises or is suspected of comprising the nucleic acids of interest. The solid support comprises two or more support capture probes, each of which is provided at a selected position on the solid support. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support. Each nucleic acid of interest can thus, by hybridizing to its corresponding subset of n target capture probes which are in turn hybridized to a corresponding support capture probe, be associated with, e.g., a known, predetermined location on the solid support. The sample, the solid support, and the subsets of n target capture probes are contacted, any nucleic acid of interest present in the sample is hybridized to its corresponding subset of n target capture probes, and the subset of n target capture probes is hybridized to its corresponding support capture probe. The hybridizing the nucleic acid of interest to the n target capture probes and the n target capture probes to the corresponding support capture probe captures the nucleic acid on the solid support at the selected position with which the target capture probes are associated.

Hybridizing the subset of n target capture probes to the corresponding support capture probe is optionally performed at a hybridization temperature which is greater than a melting temperature $T_m$ of a complex between each individual target capture probe and its corresponding support capture probe.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, type of particles, label configuration, source of the sample and/or nucleic acids, and/or the like.

Yet another general class of embodiments provides a composition that includes a solid support comprising two or more support capture probes, each of which is provided at a selected position on the solid support, and two or more subsets of n target capture probes, wherein n is at least two. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, type of particles, label configuration, source of the sample and/or nucleic acids, and/or the like.

Another general class of embodiments provides a kit for capturing two or more nucleic acids of interest. The kit includes a solid support comprising two or more support capture probes, each of which is provided at a selected position on the solid support, and two or more subsets of n target capture probes, wherein n is at least two, packaged in one or more containers. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, type of particles, label configuration, source of the sample and/or nucleic acids, and/or the like.

Figure 1D:
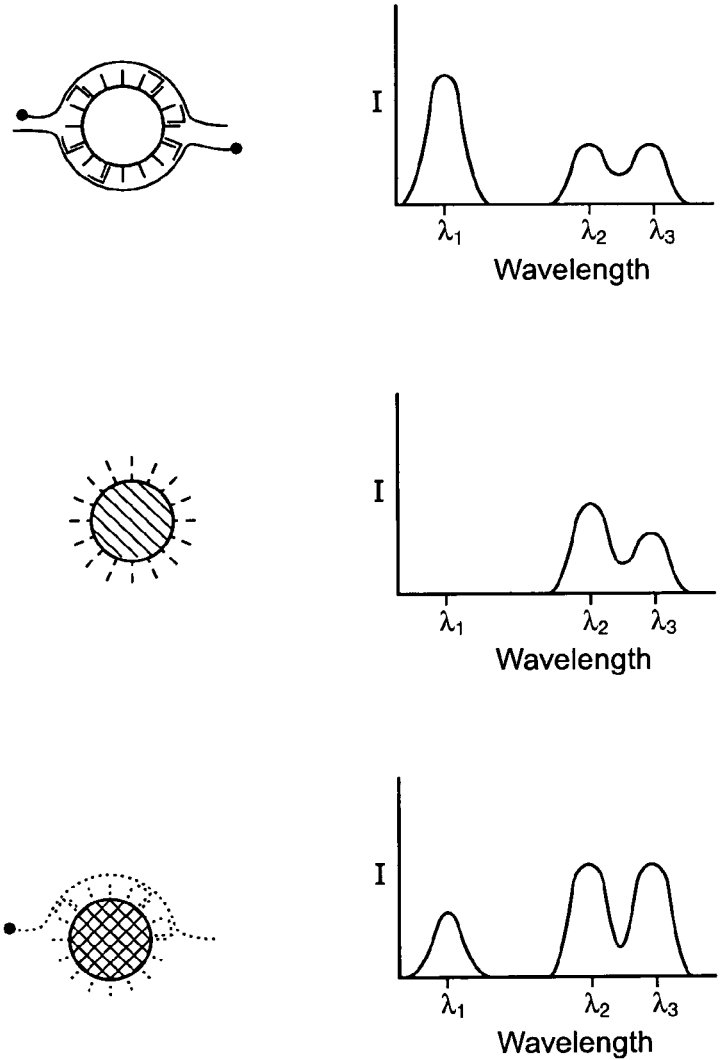
FIG. 1 Panels A-D schematically depict multiplex capture and detection of nucleic acids, where the nucleic acids of interest are captured on distinguishable subsets of microspheres and then detected.

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York), as well as in Ausubel, infra.

The "$T_m$" (melting temperature) of a nucleic acid duplex under specified conditions (e.g., relevant assay conditions) is the temperature at which half of the base pairs in a population of the duplex are disassociated and half are associated. The $T_m$ for a particular duplex can be calculated and/or measured, e.g., by obtaining a thermal denaturation curve for the duplex (where the $T_m$ is the temperature corresponding to the midpoint in the observed transition from double-stranded to single-stranded form).

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "target capture probe" is a polynucleotide that is capable of hybridizing to a nucleic acid of interest and to a support capture probe. The target capture probe typically has a first polynucleotide sequence U-1, which is complementary to the support capture probe, and a second polynucleotide sequence U-3, which is complementary to a polynucleotide sequence of the nucleic acid of interest. Sequences U-1 and U-3 are typically not complementary to each other. The target capture probe is preferably single-stranded.

A "support capture probe" is a polynucleotide that is capable of hybridizing to at least one target capture probe and that is tightly bound (e.g., covalently or noncovalently, directly or through a linker, e.g., streptavidin-biotin or the like) to a solid support, a spatially addressable solid support, a slide, a particle, a microsphere, or the like. The support capture probe typically comprises at least one polynucleotide sequence U-2 that is complementary to polynucleotide sequence U-1 of at least one target capture probe. The support capture probe is preferably single-stranded.

A "label" is a moiety that facilitates detection of a molecule. Common labels in the context of the present invention include fluorescent, luminescent, light-scattering, and/or colorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "microsphere" is a small spherical, or roughly spherical, particle. A microsphere typically has a diameter less than about 1000 micrometers (e.g., less than about 100 micrometers, optionally less than about 10 micrometers).

A "microorganism" is an organism of microscopic or sub-microscopic size. Examples include, but are not limited to, bacteria, fungi, yeast, protozoans, microscopic algae (e.g., unicellular algae), viruses (which are typically included in this category although they are incapable of growth and reproduction outside of host cells), subviral agents, viroids, and mycoplasma.

A variety of additional terms are defined or otherwise characterized herein.

DETAILED DESCRIPTION

The present invention provides methods, compositions, and kits for multiplex capture of nucleic acids. A particular nucleic acid of interest is captured to a surface through cooperative hybridization of multiple target capture probes to the nucleic acid. Each of the target capture probes has a first polynucleotide sequence that can hybridize to the target nucleic acid and a second polynucleotide sequence that can hybridize to a support capture probe that is bound to the surface. The temperature and the stability of the complex between a single target capture probe and its corresponding support capture probe can be controlled such that binding of a single target capture probe to a nucleic acid and to the support capture probe is not sufficient to stably capture the nucleic acid on the surface to which the support capture probe is bound, whereas simultaneous binding of two or more target capture probes to a nucleic acid can capture it on the surface. Requiring such cooperative hybridization of multiple target capture probes for capture of each nucleic acid of interest results in high specificity and low background from cross-hybridization of the target capture probes with other, non-target nucleic acids. Such low background and minimal cross-hybridization are typically substantially more difficult to achieve in multiplex than a single-plex capture of nucleic acids, because the number of potential nonspecific interactions are greatly increased in a multiplex experiment due to the increased number of probes used (e.g., the greater number of target capture probes). Requiring multiple simultaneous target capture probe-support capture probe interactions for the capture of a target nucleic acid minimizes the chance that nonspecific capture will occur, even when some nonspecific target-target capture probe and/or target capture probe-support capture probe interactions do occur.

The methods of the invention can be used for multiplex capture of two or more nucleic acids simultaneously, for example, from even complex samples, without requiring prior purification of the nucleic acids, when the nucleic acids are present at low concentration, and/or in the presence of other, highly similar nucleic acids. In one aspect, the methods involve capture of the nucleic acids to particles (e.g., distinguishable subsets of microspheres), while in another aspect, the nucleic acids are captured to a spatially addressable solid support. After capture, the nucleic acids are optionally detected, amplified, isolated, and/or the like. Compositions, kits, and systems related to the methods are also provided.

Methods

A first general class of embodiments includes methods of capturing two or more nucleic acids of interest. In the methods, a sample, a pooled population of particles, and two or more subsets of n target capture probes, wherein n is at least two, are provided. The sample comprises or is suspected of comprising the nucleic acids of interest. The pooled population of particles includes two or more subsets of particles. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. Preferably, a plurality of the particles in each subset are distinguishable from a plurality of the particles in every other subset. (Typically, substantially all of the particles in each subset are distinguishable from substantially all of the particles in every other subset.) Each nucleic acid of interest can thus, by hybridizing to its corresponding subset of n target capture probes which are in turn hybridized to a corresponding support capture probe, be associated with an identifiable subset of the particles. Alternatively, the particles in the various subsets need not be distinguishable from each other (for example, in embodiments in which any nucleic acid of interest present is to be isolated, amplified, and/or detected, without regard to its identity, following its capture on the particles.)

The sample, the pooled population of particles, and the subsets of n target capture probes are contacted, any nucleic acid of interest present in the sample is hybridized to its corresponding subset of n target capture probes, and the subset of n target capture probes is hybridized to its corresponding support capture probe. The hybridizing the nucleic acid of interest to the n target capture probes and the n target capture probes to the corresponding support capture probe captures the nucleic acid on the subset of particles with which the target capture probes are associated. The hybridizing the subset of n target capture probes to the corresponding support capture probe is performed at a hybridization temperature which is greater than a melting temperature $T_m$ of a complex between each individual target capture probe and its corresponding support capture probe. Binding of a single target capture probe to its corresponding nucleic acid (or to an extraneous nucleic acid) and support capture probe is thus typically insufficient to capture the nucleic acid on the corresponding subset of particles. It will be evident that the hybridization temperature is typically less than a $T_m$ of a complex between the nucleic acid of interest, all n corresponding target capture probes, and the corresponding support capture probe.

The methods are useful for multiplex capture of nucleic acids, optionally highly multiplex capture. Thus, the two or more nucleic acids of interest (i.e., the nucleic acids to be captured) optionally comprise five or more, 10 or more, 20 or more, 30 or more, 40 or more, 50 or more, or even 100 or more nucleic acids of interest. A like number of subsets of particles and subsets of target capture probes are typically provided; thus, the two or more subsets of particles can comprise five or more, 10 or more, 20 or more, 30 or more, 40 or more, 50 or more, or even 100 or more subsets of particles, while the two or more subsets of n target capture probes can comprise five or more, 10 or more, 20 or more, 30 or more, 40 or more, 50 or more, or even 100 or more subsets of n target capture probes.

Essentially any suitable particles, e.g., particles to which support capture probes can be attached and which optionally have distinguishable characteristics, can be used. For example, in one preferred class of embodiments, the particles are microspheres. The microspheres of each subset can be distinguishable from those of the other subsets, e.g., on the basis of their fluorescent emission spectrum, their diameter, or a combination thereof. For example, the microspheres of each subset can be labeled with a unique fluorescent dye or mixture of such dyes, quantum dots with distinguishable emission spectra, and/or the like. As another example, the particles of each subset can be identified by an optical barcode, unique to that subset, present on the particles.

The particles optionally have additional desirable characteristics. For example, the particles can be magnetic or paramagnetic, which provides a convenient means for separating the particles from solution, e.g., to simplify separation of the particles from any materials not bound to the particles.

As noted, each of the two or more subsets of target capture probes includes n target capture probes, where n is at least two. Preferably, n is at least three, and n can be at least four or at least five or more. Typically, but not necessarily, n is at most ten. For example, n can be between three and ten, e.g., between five and ten or between five and seven, inclusive. Use of fewer target capture probes can be advantageous, for example, in embodiments in which nucleic acids of interest are to be specifically captured from samples including other nucleic acids with sequences very similar to that of the nucleic acids of interest. In other embodiments (e.g., embodiments in which capture of as much of the nucleic acid as possible is desired), however, n can be more than 10, e.g., between 20 and 50. n can be the same for all of the subsets of target capture probes, but it need not be; for example, one subset can include three target capture probes while another subset includes five target capture probes. The n target capture probes in a subset preferably hybridize to nonoverlapping polynucleotide sequences in the corresponding nucleic acid of interest. The nonoverlapping polynucleotide sequences can, but need not be, consecutive within the nucleic acid of interest.

Each target capture probe is capable of hybridizing to its corresponding support capture probe. The target capture probe typically includes a polynucleotide sequence U-1 that is complementary to a polynucleotide sequence U-2 in its corresponding support capture probe. In one aspect, U-1 and U-2 are 20 nucleotides or less in length. In one class of embodiments, U-1 and U-2 are between 9 and 17 nucleotides in length (inclusive), preferably between 12 and 15 nucleotides (inclusive). For example, U-1 and U-2 can be 14, 15, 16, or 17 nucleotides in length, or they can be between 9 and 13 nucleotides in length (e.g., for lower hybridization temperatures, e.g., hybridization at room temperature).

The support capture probe can include polynucleotide sequence in addition to U-2, or U-2 can comprise the entire polynucleotide sequence of the support capture probe. For example, each support capture probe optionally includes a linker sequence between the site of attachment of the support capture probe to the particles and sequence U-2 (e.g., a linker sequence containing 8 Ts, as just one possible example).

It will be evident that the amount of overlap between each individual target capture probe and its corresponding support capture probe (i.e., the length of U-1 and U-2) affects the $T_m$ of the complex between that target capture probe and support capture probe, as does, e.g., the GC base content of sequences U-1 and U-2. Typically, all the support capture probes are the same length (as are sequences U-1 and U-2) from subset of particles to subset. However, depending, e.g., on the precise nucleotide sequence of U-2, different support capture probes optionally have different lengths and/or different length sequences U-2, to achieve the desired $T_m$. Different support capture probe-target capture probe complexes optionally have the same or different $T_m$s.

It will also be evident that the number of target capture probes required for stable capture of a nucleic acid depends, in part, on the amount of overlap between the target capture probes and the support capture probe (i.e., the length of U-1 and U-2). For example, if n is 5-7 for a 14 nucleotide overlap, n could be 3-5 for a 15 nucleotide overlap or 2-3 for a 16 nucleotide overlap.

As noted, the hybridizing the subset of n target capture probes to the corresponding support capture probe is performed at a hybridization temperature which is greater than a melting temperature $T_m$ of a complex between each individual target capture probe and its corresponding support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Stable capture of nucleic acids of interest, e.g., while minimizing capture of extraneous nucleic acids (e.g., those to which n−1 or fewer of the target capture probes bind) can be achieved, for example, by balancing n (the number of target capture probes), the amount of overlap between the target capture probes and the support capture probe (the length of U-1 and U-2), and/or the stringency of the conditions under which the target capture probes, the nucleic acids, and the support capture probes are hybridized.

Appropriate combinations of n, amount of complementarity between the target capture probes and the support capture probe, and stringency of hybridization can, for example, be determined experimentally by one of skill in the art. For example, a particular value of n and a particular set of hybridization conditions can be selected, while the number of nucleotides of complementarity between the target capture probes and the support capture probe is varied until hybridization of the n target capture probes to a nucleic acid captures the nucleic acid while hybridization of a single target capture probe does not efficiently capture the nucleic acid. Similarly, n, amount of complementarity, and stringency of hybridization can be selected such that the desired nucleic acid of interest is captured while other nucleic acids present in the sample are not efficiently captured. Stringency can be controlled, for example, by controlling the formamide concentration, chaotropic salt concentration, salt concentration, pH, organic solvent content, and/or hybridization temperature.

As noted, the $T_m$ of any nucleic acid duplex can be directly measured, using techniques well known in the art. For example, a thermal denaturation curve can be obtained for the duplex, the midpoint of which corresponds to the $T_m$. It will be evident that such denaturation curves can be obtained under conditions having essentially any relevant pH, salt concentration, solvent content, and/or the like.

The $T_m$ for a particular duplex (e.g., an approximate $T_m$) can also be calculated. For example, the $T_m$ for an oligonucleotide-target duplex can be estimated using the following algorithm, which incorporates nearest neighbor thermodynamic parameters: $Tm\ (Kelvin) = \Delta H^\circ/(\Delta S^\circ + R\ \ln C_t)$, where the changes in standard enthalpy ($\Delta H^\circ$) and entropy ($\Delta S^\circ$) are calculated from nearest neighbor thermodynamic parameters (see, e.g., SantaLucia (1998) "A unified view of polymer, dumbbell, and oligonucleotide DNA nearest-neighbor thermodynamics" Proc. Natl. Acad. Sci. USA 95:1460-1465, Sugimoto et al. (1996) "Improved thermodynamic parameters and helix initiation factor to predict stability of DNA duplexes" Nucleic Acids Research 24: 4501-4505, Sugimoto et al. (1995) "Thermodynamic parameters to predict stability of RNA/DNA hybrid duplexes" Biochemistry 34:11211-11216, and et al. (1998) "Thermodynamic parameters for an expanded nearest-neighbor model for formation of RNA duplexes with Watson-Crick base pairs" Biochemistry 37: 14719-14735), R is the ideal gas constant (1.987 cal·K$^{-1}$mole$^{-1}$), and $C_t$ is the molar concentration of the oligonucleotide. The calculated $T_m$ is optionally corrected for salt concentration, e.g., Na$^+$ concentration, using the formula $1/T_m$ (Na$^+$)$=1/T_m$ (1M)$+(4.29f\ (G \cdot C) - 3.95) \times 10^{-5}\ \ln$ [Na$^+$]$+9.40 \times 10^{-6}\ \ln^2$ [Na$^+$]. See, e.g., Owczarzy et al. (2004) "Effects of sodium ions on DNA duplex oligomers: Improved predictions of melting temperatures" Biochemistry 43:3537-3554 for further details. A web calculator for estimating Tm using the above algorithms is available on the internet at scitools.idtdna.com/analyzer/oligocalc.asp. Other algorithms for calculating Tm are known in the art and are optionally applied to the present invention.

For a given nucleic acid of interest, the corresponding target capture probes are preferably complementary to physically distinct, nonoverlapping sequences in the nucleic acid of interest, which are preferably, but not necessarily, contiguous. The $T_m$s of the individual target capture probe-nucleic acid complexes are preferably greater than the hybridization temperature, e.g., by 5° C. or 10° C. or preferably by 15° C. or more, such that these complexes are stable at the hybridization temperature. Sequence U-3 for each target capture probe is typically (but not necessarily) about 17-35 nucleotides in length, with about 30-70% GC content. Potential target capture probe sequences (e.g., potential sequences U-3) are optionally examined for possible interactions with non-corresponding nucleic acids of interest, repetitive sequences (such as polyC or polyT, for example), any detection probes used to detect the nucleic acids of interest, and/or any relevant genomic sequences, for example; sequences expected to cross-hybridize with undesired nucleic acids are typically not selected for use in the target support capture probes. Examination can be, e.g., visual (e.g., visual examination for complementarity), computational (e.g., computation and comparison of percent sequence identity and/or binding free energies; for example, sequence comparisons can be performed using BLAST software publicly available through the National Center for Biotechnology Information on the world wide web at ncbi.nlm.nih.gov), and/or experimental (e.g., cross-hybridization experiments). Support capture probe sequences are preferably similarly examined, to ensure that the polynucleotide sequence U-1 complementary to a particular support capture probe's sequence U-2 is not expected to cross-hybridize with any of the other support capture probes that are to be associated with other subsets of particles. See, e.g., Example 1 herein.

In one class of embodiments, contacting the sample, the pooled population of particles, and the subsets of n target capture probes comprises combining the sample with the subsets of n target capture probes to form a mixture, and then combining the mixture with the pooled population of particles. In this class of embodiments, the target capture probes typically hybridize first to the corresponding nucleic acid of interest and then to the corresponding particle-associated support capture probe. The hybridizations can, however, occur simultaneously or even in the opposite order. Thus, in another exemplary class of embodiments, contacting the sample, the pooled population of particles, and the subsets of n target capture probes comprises combining the sample, the subsets of target capture probes, and the pooled population of particles.

As noted, the nucleic acids are optionally detected, amplified, isolated, and/or the like after capture. Thus, in one aspect, a plurality of the particles in each subset are distinguishable from a plurality of the particles in every other subset, and the methods include determining which subsets of particles have a nucleic acid of interest captured on the particles, thereby indicating which of the nucleic acids of interest were present in the sample. For example, in one class of embodiments, each of the nucleic acids of interest comprises a label (including, e.g., one or two or more labels per molecule), and determining which subsets of particles have a nucleic acid of interest captured on the particles comprises detecting a signal from the label. At least a portion of the particles from each subset can be identified and the presence or absence of the label detected on those particles. Since a correlation exists between a particular subset of particles and a particular nucleic acid of interest, which subsets of particles have the label present indicates which of the nucleic acids of interest were present in the sample. In one class of embodiments, the label is covalently associated with the nucleic acid. For example, a fluorescent label can be incorporated into the nucleic acid using a chemical or enzymatic labeling technique. In other embodiments, the nucleic acid is configured to bind the label; for example, a biotinylated nucleic acid can bind a streptavidin-associated label.

The label can be essentially any convenient label that directly or indirectly provides a detectable signal. In one aspect, the label is a fluorescent label (e.g., a fluorophore or quantum dot, e.g., Cy3 or Cy5). Detecting the presence of the label on the particles thus comprises detecting a fluorescent signal from the label. Fluorescent emission by the label is typically distinguishable from any fluorescent emission by the particles, e.g., microspheres, and many suitable fluorescent label-fluorescent microsphere combinations are possible. As other examples, the label can be a luminescent label, a light-scattering label (e.g., colloidal gold particles), or an enzyme (e.g., HRP).

The methods can optionally be used to quantitate the amounts of the nucleic acids of interest present in the sample. For example, in one class of embodiments, an intensity of the signal from the label is measured, e.g., for each subset of particles, and correlated with a quantity of the corresponding nucleic acid of interest present.

As another example, in one class of embodiments, at least one detection probe (a polynucleotide comprising a label or configured to bind a label) is provided for each nucleic acid of interest and hybridized to any nucleic acid of interest captured on the particles. As described above, determining which subsets of particles have a nucleic acid of interest captured on the particles then comprises detecting a signal from the label (e.g., a fluorescent label).

As yet another example, in one class of embodiments, determining which subsets of particles have a nucleic acid of interest captured on the particles comprises amplifying any nucleic acid of interest captured on the particles. A wide variety of techniques for amplifying nucleic acids are known in the art, including, but not limited to, PCR (polymerase chain reaction), rolling circle amplification, and transcription mediated amplification. (See, e.g., Hatch et al. (1999) "Rolling circle amplification of DNA immobilized on solid surfaces and its application to multiplex mutation detection" Genet Anal. 15:35-40; Baner et al. (1998) "Signal amplification of padlock probes by rolling circle replication" Nucleic Acids Res. 26:5073-8; and Nallur et al. (2001) "Signal amplification by rolling circle amplification on DNA microarrays" Nucleic Acids Res. 29:E118.) A labeled primer and/or labeled nucleotides are optionally incorporated during amplification. In other embodiments, the nucleic acids of interest captured on the particles are detected and/or amplified without identifying the subsets of particles and/or the nucleic acids (e.g., in embodiments in which the subsets of particles are not distinguishable).

In one class of embodiments, one or more subsets of particles is isolated, whereby any nucleic acid of interest captured on the particles is isolated. The isolated nucleic acid can optionally be removed from the particles and/or subjected to further manipulation, if desired (e.g., amplification by PCR or the like). The particles from various subsets can be distinguishable or indistinguishable.

At any of various steps, materials not captured on the particles are optionally separated from the particles. For example, after the target capture probes, nucleic acids, and particle-bound support capture probes are hybridized, the particles are optionally washed to remove unbound nucleic acids and target capture probes.

An exemplary embodiment is schematically illustrated in FIG. 1. Panel A illustrates three distinguishable subsets of microspheres 101, 102, and 103, which have associated therewith support capture probes 104, 105, and 106, respectively. Each support capture probe includes a sequence U-2 (150), which is different from subset to subset of microspheres. The three subsets of microspheres are combined to form pooled population 108 (Panel B). A subset of three target capture probes is provided for each nucleic acid of interest; subset 111 for nucleic acid 114, subset 112 for nucleic acid 115 which is not present, and subset 113 for nucleic acid 116. Each target capture probe includes sequences U-1 (151, complementary to the respective support capture probe's sequence U-2) and U-3 (152, complementary to a sequence in the corresponding nucleic acid of interest). Each nucleic acid of interest includes at least one label 117. Non-target nucleic acids 130 are also present in the sample of nucleic acids.

Nucleic acids 114 and 116 are hybridized to their corresponding subset of target capture probes (111 and 113, respectively), and the target capture probes are hybridized to the corresponding support capture probes (104 and 106, respectively), capturing nucleic acids 114 and 116 on microspheres 101 and 103, respectively (Panel C). Materials not captured on the microspheres (e.g., target capture probes 112, nucleic acids 130, etc.) are optionally separated from the microspheres by washing. Microspheres from each subset are identified, e.g., by their fluorescent emission spectrum ($\lambda_2$ and $\lambda_3$, Panel D), and the presence or absence of the label on each subset of microspheres is detected ($\lambda_1$, Panel D). Since each nucleic acid of interest is associated with a distinct subset of microspheres, the presence of the label on a given subset of microspheres correlates with the presence of the corresponding nucleic acid in the original sample.

As depicted in FIG. 1, each support capture probe typically includes a single sequence U-2 and thus hybridizes to a single target capture probe. Optionally, however, a support capture probe can include two or more sequences U-2 and hybridize to two or more target capture probes. Similarly, as depicted, each of the target capture probes in a particular subset typically includes an identical sequence U-1, and thus only a single support capture probe is needed for each subset of particles; however, different target capture probes within a subset optionally include different sequences U-1 (and thus hybridize to different sequences U-2, within a single support capture probe or different support capture probes on the surface of the corresponding subset of particles).

The methods can be used to capture the nucleic acids of interest from essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen. As additional examples, the two or more nucleic acids of interest can comprise two or more mRNAs, bacterial and/or viral genomic RNAs and/or DNAs (double-stranded or single-stranded), plasmid or other extragenomic DNAs, or other nucleic acids derived from microorganisms (pathogenic or otherwise). The nucleic acids can be purified, partially purified, or unpurified. The nucleic acids are optionally, but not necessarily, produced by an amplification reaction (e.g., the nucleic acids can be the products of reverse transcription or PCR). It will be evident that double-stranded nucleic acids of interest will typically be denatured before hybridization with target capture probes.

Due to cooperative hybridization of multiple target capture probes to a nucleic acid of interest, for example, even nucleic acids present at low concentration can be captured. Thus, in one class of embodiments, at least one of the nucleic acids of interest is present in the sample in a non-zero amount of 200 attomole (amol) or less, 150 amol or less, 100 amol or less, 50 amol or less, 10 amol or less, 1 amol or less, or even 0.1 amol or less, 0.01 amol or less, 0.001 amol or less, or 0.0001 amol or less. Similarly, two nucleic acids of interest can be captured simultaneously, even when they differ in concentration by 1000-fold or more in the sample. The methods are thus extremely versatile.

Capture of a particular nucleic acid is optionally quantitative. Thus, in one exemplary class of embodiments, the sample includes a first nucleic acid of interest, and at least 30%, at least 50%, at least 80%, at least 90%, at least 95%, or even at least 99% of a total amount of the first nucleic acid present in the sample is captured on a first subset of particles. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the sample comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the sample, is captured on a first subset of particles, while the second nucleic acid comprises 1% or less of a total amount of nucleic acid captured on the first subset of particles (e.g., 0.5% or less, 0.2% or less, or even 0.1% or less). The second nucleic acid can be another nucleic acid of interest or simply any nucleic acid. Typically, target capture probes are chosen that hybridize to regions of the first nucleic acid having the greatest sequence difference from the second nucleic acid.

Figure 2:
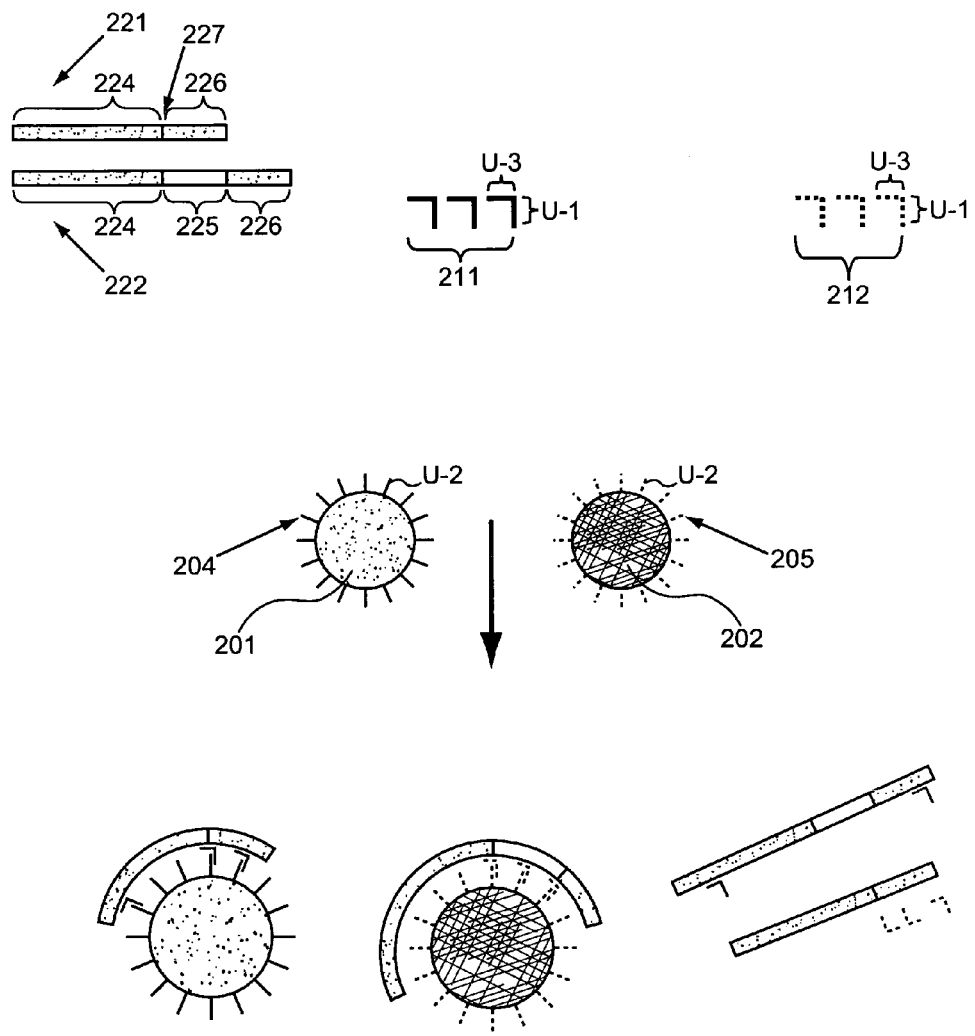
FIG. 2 schematically depicts an exemplary embodiment in which two splice variants are specifically captured on distinguishable subsets of microspheres.

As just one example of how closely related nucleic acids can be differentially captured using the methods of the invention, different splice variants of a given mRNA can be selectively captured. Thus, in one class of embodiments, the sample comprises a first nucleic acid of interest and a second nucleic acid, where the first nucleic acid is a first splice variant and the second nucleic acid is a second splice variant of the given mRNA. A first subset of n target capture probes is capable of hybridizing to the first splice variant, of which at most n−1 target capture probes are capable of hybridizing to the second splice variant. Optionally, at least 80% or more, 90% or more, or 95% or more of the first splice variant is captured on a first subset of particles while at most 10% or less, 5% or less, 3% or less, or 1% or less of the second splice variant is captured on the first subset of particles. Preferably, hybridization of the n target capture probes to the first splice variant captures the first splice variant on a first subset of particles while hybridization of the at most n−1 target capture probes to the second splice variant does not capture the second splice variant on the first subset of particles. An exemplary embodiment illustrating capture of two splice variants is schematically depicted in FIG. 2. In this example, three target capture probes 211 hybridize to first splice variant 221, one to each exon (224 and 226) and one to splice junction 227 (the only sequence found in first splice variant 221 and not also found in second splice variant 222); two of these bind to second splice variant 222. Similarly, three target capture probes 212 bind to second splice variant 222, one to intron 225 and one to each of the splice junctions; none of these bind to first splice variant 221. Through cooperative hybridization of the target capture probes to the splice variants and to the corresponding support capture probes (204 and 205), splice variants 221 and 222 are each captured specifically only on the corresponding subset of microspheres (201 and 202, respectively). Optionally, for any nucleic acid, hybridization of a first subset of n target capture probes to a first nucleic acid captures the first nucleic acid on a first subset of particles while hybridization of at most n−1 of the target capture probes to a second nucleic acid does not capture the second nucleic acid on the first subset of particles.

It will be evident that nucleic acids that do not have 100% identical sequences are alternatively optionally captured on the same subset of particles, if desired. For example, a first and a second nucleic acid are optionally both captured on a first subset of particles, through binding of the same or different subsets of target capture probes. The first and second nucleic acids can be closely related; for example, splice variants of a particular mRNA, different alleles of a gene, somatic mutations, homologs, or the like. Similarly, it will be evident that a single type of particle bearing a single support capture probe (rather than multiple distinguishable subsets of particles bearing different support capture probes) can be used to capture multiple nucleic acids, e.g., in aspects in which a few specific target nucleic acids are to be isolated and/or in which individual targets need not be identified.

A support capture probe and/or target capture probe optionally comprises at least one non-natural nucleotide. For example, a support capture probe and the corresponding target capture probe optionally comprise, at complementary positions, at least one pair of non-natural nucleotides that base pair with each other but that do not Watson-Crick base pair with the bases typical to biological DNA or RNA (i.e., A, C, G, T, or U). Examples of nonnatural nucleotides include, but are not limited to, Locked NucleicAcid™ nucleotides (available from Exiqon A/S, on the world wide web at (www.)exiqon.com; see, e.g., SantaLucia Jr. (1998) Proc Natl Acad Sci 95:1460-1465) and isoG, isoC, and other nucleotides used in the AEGIS system (Artificially Expanded Genetic Information System, available from EraGen Biosciences, (www.)eragen.com; see, e.g., U.S. Pat. Nos. 6,001,983, 6,037,120, and 6,140,496). Use of such non-natural base pairs (e.g., isoG-isoC base pairs) in the support capture probes and target capture probes can, for example, decrease cross hybridization, or it can permit use of shorter support capture probe and target capture probes when the non-natural base pairs have higher binding affinities than do natural base pairs.

The preceding embodiments include capture of the nucleic acids of interest on particles. Alternatively, the nucleic acids can be captured at different positions on a non-particulate, spatially addressable solid support. Accordingly, another general class of embodiments includes methods of capturing two or more nucleic acids of interest. In the methods, a sample, a solid support, and two or more subsets of n target capture probes, wherein n is at least two, are provided. The sample comprises or is suspected of comprising the nucleic acids of interest. The solid support comprises two or more support capture probes, each of which is provided at a selected position on the solid support. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support. Each nucleic acid of interest can thus, by hybridizing to its corresponding subset of n target capture probes which are in turn hybridized to a corresponding support capture probe, be associated with, e.g., a known, predetermined location on the solid support. The sample, the solid support, and the subsets of n target capture probes are contacted, any nucleic acid of interest present in the sample is hybridized to its corresponding subset of n target capture probes, and the subset of n target capture probes is hybridized to its corresponding support capture probe. The hybridizing the nucleic acid of interest to the n target capture probes and the n target capture probes to the corresponding support capture probe captures the nucleic acid on the solid support at the selected position with which the target capture probes are associated.

The hybridizing the subset of n target capture probes to the corresponding support capture probe is typically performed at a hybridization temperature which is greater than a melting temperature $T_m$ of a complex between each individual target capture probe and its corresponding support capture probe. For example, the hybridization temperature can be about 5° C. or more greater than the $T_m$, e.g., about 7° C. or more, about 10° C. or more, about 12° C. or more, about 15° C. or more, about 17° C. or more, or even about 20° C. or more greater than the $T_m$.

The methods are useful for multiplex capture of nucleic acids, optionally highly multiplex capture. Thus, the two or more nucleic acids of interest (i.e., the nucleic acids to be captured) optionally comprise five or more, 10 or more, 20 or more, 30 or more, 40 or more, 50 or more, 100 or more, $10^3$ or more, or $10^4$ or more nucleic acids of interest. A like number of selected positions on the solid support and subsets of target capture probes are provided; thus, the two or more selected positions can comprise five or more, 10 or more, 20 or more, 30 or more, 40 or more, 50 or more, 100 or more, $10^3$ or more, or $10^4$ or more selected positions, while the two or more subsets of n target capture probes can comprise five or more, 10 or more, 20 or more, 30 or more, 40 or more, 50 or more, 100 or more, $10^3$ or more, or $10^4$ or more subsets of n target capture probes.

The solid support typically has a planar surface and is typically rigid, but essentially any spatially addressable solid support can be adapted to the practice of the present invention. Exemplary materials for the solid support include, but are not limited to, glass, silicon, silica, quartz, plastic, polystyrene, nylon, and nitrocellulose. As just one example, an array of support capture probes can be formed at selected positions on a glass slide as the solid support.

As for the embodiments described above, the nucleic acids are optionally detected, amplified, isolated, and/or the like after capture. Thus, in one aspect, the methods include determining which positions on the solid support have a nucleic acid of interest captured at that position, thereby indicating which of the nucleic acids of interest were present in the sample. For example, in one class of embodiments, each of the nucleic acids of interest comprises a label (including, e.g., one or two or more labels per molecule), and determining which positions on the solid support have a nucleic acid of interest captured at that position comprises detecting a signal from the label, e.g., at each position. Since a correlation exists between a particular position on the support and a particular nucleic acid of interest, which positions have a label present indicates which of the nucleic acids of interest were present in the sample. In one class of embodiments, the label is covalently associated with the nucleic acid. In other embodiments, the nucleic acid is configured to bind the label; for example, a biotinylated nucleic acid can bind a streptavidin-associated label.

The methods can optionally be used to quantitate the amounts of the nucleic acids of interest present in the sample. For example, in one class of embodiments, an intensity of the signal from the label is measured, e.g., for each of the selected positions, and correlated with a quantity of the corresponding nucleic acid of interest present.

As another example, in one class of embodiments, at least one detection probe (a polynucleotide comprising a label or configured to bind a label) is provided for each nucleic acid of interest and hybridized to any nucleic acid of interest captured on the support. As described above, determining which positions on the support have a nucleic acid of interest captured on the support then comprises detecting a signal from the label. As yet another example, in one class of embodiments, determining which positions on the solid support have a nucleic acid of interest captured at that position comprises amplifying any nucleic acid of interest captured on the solid support, as for the embodiments described above.

At any of various steps, materials not captured on the solid support are optionally separated from the solid support. For example, after the target capture probes, nucleic acids, and support-bound support capture probes are hybridized, the solid support is optionally washed to remove unbound nucleic acids and target capture probes.

Essentially all of the features noted for the methods above apply to these embodiments as well, as relevant; for example, with respect to number of target capture probes per subset, configuration of the target capture probes and/or support capture probes, label configuration, source of the sample and/or nucleic acids, and/or the like.

For example, in one class of embodiments, contacting the sample, the solid support, and the subsets of n target capture probes comprises combining the sample with the subsets of n target capture probes to form a mixture, and then contacting the mixture with the solid support. In this class of embodiments, the target capture probes typically hybridize first to the corresponding nucleic acid of interest and then to the corresponding particle-associated support capture probe. In other embodiments, however, the hybridizations can occur simultaneously or even in the opposite order.

As for the embodiments described above, capture of a particular nucleic acid is optionally quantitative. Thus, in one exemplary class of embodiments, the sample includes a first nucleic acid of interest, and at least 30%, at least 50%, at least 80%, at least 90%, at least 95%, or even at least 99% of a total amount of the first nucleic acid present in the sample is captured at a first selected position on the solid support. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the sample comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the sample, is captured at a first selected position on the solid support, while the second nucleic acid comprises 1% or less of a total amount of nucleic acid captured at the first position (e.g., 0.5% or less, 0.2% or less, or even 0.1% or less). The second nucleic acid can be another nucleic acid of interest or simply any nucleic acid. Typically, target capture probes are chosen that hybridize to regions of the first nucleic acid having the greatest sequence difference from the second nucleic acid.

As just one example of how closely related nucleic acids can be differentially captured using the methods of the invention, different splice variants of a given mRNA can be selectively captured. Thus, in one class of embodiments, the sample comprises a first nucleic acid of interest and a second nucleic acid, where the first nucleic acid is a first splice variant and the second nucleic acid is a second splice variant of the given mRNA. A first subset of n target capture probes is capable of hybridizing to the first splice variant, of which at most n−1 target capture probes are capable of hybridizing to the second splice variant. Optionally, at least 80% or more, 90% or more, or 95% or more of the first splice variant is captured at a first selected position on the solid support while at most 10% or less, 5% or less, 3% or less, or 1% or less of the second splice variant is captured at the first position. Preferably, hybridization of the n target capture probes to the first splice variant captures the first splice variant at a first selected position on the solid support while hybridization of the at most n−1 target capture probes to the second splice variant does not capture the second splice variant at the first position.

It will be evident that nucleic acids that do not have 100% identical sequences are alternatively optionally captured at the same position of the support, if desired. For example, a first and a second nucleic acid are optionally both captured at a first position, through binding of the same or different subsets of target capture probes. The first and second nucleic acids can be closely related; for example, splice variants of a particular mRNA, different alleles of a gene, somatic mutations, homologs, or the like. Similarly, it will be evident that a single support-bound support capture probe (rather than different support capture probes at different selected positions on the support) can be used to capture multiple nucleic acids, e.g., in aspects in which a few specific target nucleic acids are to be isolated and/or in which individual targets need not be identified.

Figure 3:
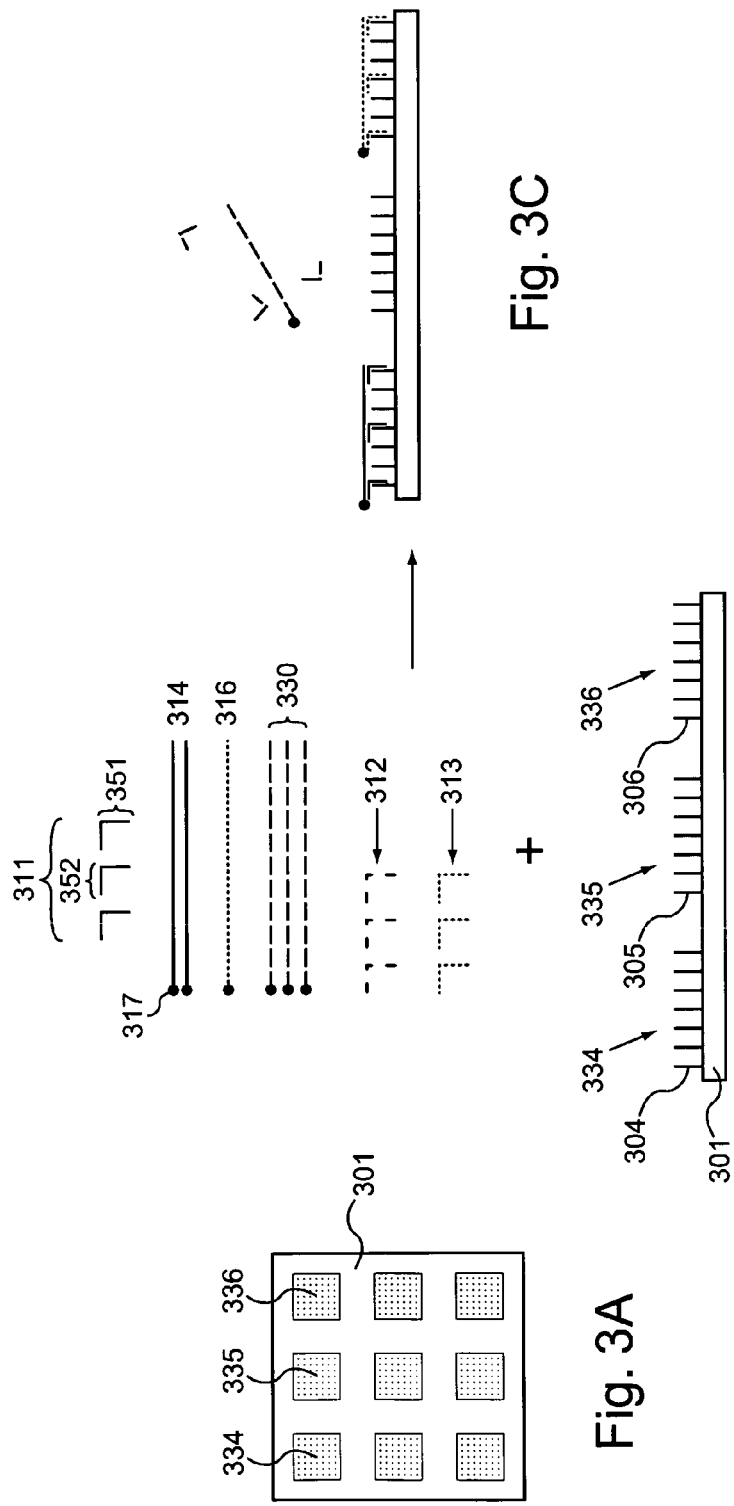
FIG. 3 Panels A-C schematically depict multiplex capture of nucleic acids, where the nucleic acids of interest are captured at selected positions on a solid support. Panel A shows a top view of the solid support, while Panels B-C show the support in cross-section.

An exemplary embodiment is schematically illustrated in FIG. 3. Panel A depicts solid support 301 having nine support capture probes provided on it at nine selected positions (e.g., 334-336). Panel B depicts a cross section of solid support 301, with distinct support capture probes 304, 305, and 306 at different selected positions on the support (334, 335, and 336, respectively). A subset of target capture probes is provided for each nucleic acid of interest. Only three subsets are depicted; subset 311 for nucleic acid 314, subset 312 for nucleic acid 315 which is not present, and subset 313 for nucleic acid 316. Each target capture probe includes sequences U-1 (351, complementary to the respective support capture probe's sequence U-2) and U-3 (352, complementary to a sequence in the corresponding nucleic acid of interest). Each nucleic acid of interest includes at least one label 317. Non-target nucleic acids 330 are also present in the sample of nucleic acids.

Nucleic acids 314 and 316 are hybridized to their corresponding subset of target capture probes (311 and 313, respectively), and the target capture probes are hybridized to the corresponding support capture probes (304 and 306, respectively), capturing nucleic acids 314 and 316 at selected positions 334 and 336, respectively (Panel C). Materials not captured on the solid support (e.g., target capture probes 312, nucleic acids 330, etc.) are optionally removed by washing the support, and the presence or absence of the label at each position on the solid support is detected. Since each nucleic acid of interest is associated with a distinct position on the support, the presence of the label at a given position on the support correlates with the presence of the corresponding nucleic acid in the original sample.

The methods of the present invention offer a number of advantages. For example, a single array of support capture probes at selected positions on a solid support can be manufactured, and this single array can be used to capture essentially any desired group of nucleic acids of interest simply by synthesizing appropriate subsets of target capture probes. A new array need not be manufactured for each new group of nucleic acids to be captured, unlike conventional microarray technologies in which arrays of target-specific probes attached to a solid support are utilized, necessitating the manufacture of a new array for each new group of target nucleic acids to be captured and detected. Similarly, a single population of subsets of particles comprising support capture probes can be manufactured and used for capture of essentially any desired group of nucleic acids of interest. As previously noted, capture of a nucleic acid of interest through multiple, individually relatively weak hybridization events can provide greater specificity than does capturing the nucleic acid through hybridization with a single oligonucleotide. It can also provide greater ability to discriminate between closely related sequences than does capturing the nucleic acid through hybridization with a cDNA or other large probe.

Compositions

Compositions related to the methods are another feature of the invention. Thus, one general class of embodiments provides a composition that includes two or more subsets of particles and two or more subsets of n target capture probes, wherein n is at least two. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. When the nucleic acid of interest corresponding to a subset of n target capture probes is present in the composition and is hybridized to the subset of n target capture probes, which are hybridized to the corresponding support capture probe, the nucleic acid of interest is hybridized to the subset of n target capture probes at a hybridization temperature which is greater than a melting temperature $T_m$ of a complex between each individual target capture probe and the support capture probe.

In one preferred class of embodiments, a plurality of the particles in each subset are distinguishable from a plurality of the particles in every other subset. Typically, substantially all of the particles in each subset are distinguishable from substantially all of the particles in every other subset. Alternatively, the particles comprising the various subsets are not distinguishable.

The composition optionally includes a sample comprising or suspected of comprising at least one of the nucleic acids of interest, e.g., two or more, three or more, etc. nucleic acids. In one class of embodiments, the composition comprises one or more of the nucleic acids of interest. Each nucleic acid of interest is hybridized to its corresponding subset of n target capture probes, and the corresponding subset of n target capture probes is hybridized to its corresponding support capture probe. Each nucleic acid of interest is thus associated with a subset of the particles. The composition is maintained at the hybridization temperature.

As noted, the hybridization temperature is greater than the $T_m$ of each of the individual target capture probe-support capture probe complexes. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Essentially all of the features noted for the methods above apply to these embodiments as well, as relevant; for example, with respect to number of target capture probes per subset, configuration of the target capture probes and/or support capture probes, number of nucleic acids of interest and of subsets of particles and target capture probes, type of particles, source of the sample and/or nucleic acids, and/or the like.

As noted, even nucleic acids present at low concentration can be captured. Thus, in one class of embodiments, at least one of the nucleic acids of interest is present in the composition in a non-zero amount of 200 amol or less, 150 amol or less, 100 amol or less, 50 amol or less, 10 amol or less, 1 amol or less, or even 0.1 amol or less, 0.01 amol or less, 0.001 amol or less, or 0.0001 amol or less. Similarly, two nucleic acids of interest can be captured simultaneously, even when they differ in concentration by 1000-fold or more in the composition.

Capture of a particular nucleic acid on the particles is optionally quantitative. Thus, in one exemplary class of embodiments, the composition includes a first nucleic acid of interest, and at least 30%, at least 50%, at least 80%, at least 90%, at least 95%, or even at least 99% of a total amount of the first nucleic acid present in the composition is captured on a first subset of particles. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the composition comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the composition, is captured on a first subset of particles, while the second nucleic acid comprises 1% or less of a total amount of nucleic acid captured on the first subset of particles (e.g., 0.5% or less, 0.2% or less, or even 0.1% or less). The second nucleic acid can be another nucleic acid of interest or simply any nucleic acid. Typically, target capture probes are chosen that hybridize to regions of the first nucleic acid having the greatest sequence difference from the second nucleic acid.

In one exemplary class of embodiments in which related nucleic acids are differentially captured, the composition comprises a first nucleic acid of interest and a second nucleic acid, where the first nucleic acid is a first splice variant and the second nucleic acid is a second splice variant of a given mRNA. A first subset of n target capture probes is capable of hybridizing to the first splice variant, of which at most n−1 target capture probes are capable of hybridizing to the second splice variant. Optionally, at least 80% or more, 90% or more, or 95% or more of the first splice variant is captured on a first subset of particles while at most 10% or less, 5% or less, 3% or less, or 1% or less of the second splice variant is captured on the first subset of particles. Preferably, a first subset of n target capture probes is hybridized to the first splice variant, whereby the first splice variant is captured on a first subset of particles, and at most n−1 of the target capture probes are hybridized to the second splice variant, whereby the second splice variant is not captured on the first subset of particles.

In one class of embodiments, the composition includes one or more of the nucleic acids of interest, each of which includes a label or is configured to bind to a label. The composition optionally includes one or more of: a cell lysate, an intercellular fluid, a bodily fluid, a conditioned culture medium, a polynucleotide complementary to a nucleic acid of interest and comprising a label, or a reagent used to amplify nucleic acids (e.g., a DNA polymerase, an oligonucleotide primer, or nucleoside triphosphates).

A related general class of embodiments provides a composition comprising two or more subsets of particles, two or more subsets of n target capture probes, wherein n is at least two, and at least a first nucleic acid of interest. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. In this class of embodiments, the composition is maintained at a hybridization temperature, which hybridization temperature is greater than a melting temperature $T_m$ of a complex between each individual target capture probe and its corresponding support capture probe. The first nucleic acid of interest is hybridized to a first subset of n first target capture probes, which first target capture probes are hybridized to a first support capture probe.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, use of labeled nucleic acids of interest, additional components of the composition, source of the sample and/or nucleic acids, and/or the like. Preferably, a plurality of the particles in each subset are distinguishable from a plurality of the particles in every other subset. (Typically, substantially all of the particles in each subset are distinguishable from substantially all of the particles in every other subset.)

Another general class of embodiments provides a composition that includes a solid support comprising two or more support capture probes, each of which is provided at a selected position on the solid support, and two or more subsets of n target capture probes, wherein n is at least two. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support.

The composition optionally includes a sample comprising or suspected of comprising at least one of the nucleic acids of interest, e.g., two or more, three or more, etc. nucleic acids. In one class of embodiments, the composition includes at least a first nucleic acid of interest and is maintained at a hybridization temperature. The first nucleic acid of interest is hybridized to a first subset of n first target capture probes, which first target capture probes are hybridized to a first support capture probe; the first nucleic acid is thereby associated with a first selected position on the solid support. It will be evident that the composition optionally includes second, third, etc. nucleic acids of interest, which are likewise associated with second, third, etc. selected positions on the solid support through association with second, third, etc. subsets of target capture probes and second, third, etc. support capture probes. The hybridization temperature is greater than a melting temperature $T_m$ of a complex between each individual target capture probe and its corresponding support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Essentially all of the features noted for the embodiments above apply to these embodiments as well, as relevant; for example, with respect to number of target capture probes per subset, type of solid support, configuration of the target capture probes and/or support capture probes, number of nucleic acids of interest and of selected positions on the solid support and subsets of target capture probes, use of labeled nucleic acids of interest, additional components of the composition, source of the sample and/or nucleic acids, and/or the like.

Kits

Yet another general class of embodiments provides a kit for capturing two or more nucleic acids of interest. The kit includes two or more subsets of particles and two or more subsets of n target capture probes, wherein n is at least two, packaged in one or more containers. The particles in each subset have associated therewith a different support capture probe. Each subset of n target capture probes is capable of hybridizing to one of the nucleic acids of interest, and the target capture probes in each subset are capable of hybridizing to one of the support capture probes and thereby associating each subset of n target capture probes with a selected subset of the particles. When the nucleic acid of interest corresponding to a subset of n target capture probes is hybridized to the subset of n target capture probes, which are hybridized to the corresponding support capture probe, the nucleic acid of interest is hybridized to the subset of n target capture probes at a hybridization temperature which is greater than a melting temperature $T_m$ of a complex between each individual target capture probe and the support capture probe. The kit optionally also includes instructions for using the kit to capture and optionally detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of target capture probes per subset, configuration of the target capture probes and/or support capture probes, number of nucleic acids of interest and of subsets of particles and target capture probes, source of the sample and/or nucleic acids, type of particles, and/or the like. Preferably, a plurality of the particles in each subset are distinguishable from a plurality of the particles in every other subset. (Typically, substantially all of the particles in each subset are distinguishable from substantially all of the particles in every other subset.)

A related general class of embodiments provides a kit for capturing two or more nucleic acids of interest. The kit includes a solid support comprising two or more support capture probes, each of which is provided at a selected position on the solid support, and two or more subsets of n target capture probes, wherein n is at least two, packaged in one or more containers. Each subset of n target capture probes is capable of hybridizing to one of the nucleic acids of interest, and the target capture probes in each subset are capable of hybridizing to one of the support capture probes and thereby associating each subset of n target capture probes with a selected position on the solid support.

In one class of embodiments, when a nucleic acid of interest corresponding to a subset of n target capture probes is hybridized to the subset of n target capture probes, which are hybridized to the corresponding support capture probe, the nucleic acid of interest is hybridized to the subset of n target capture probes at a hybridization temperature which is greater than a melting temperature $T_m$ of a complex between each individual target capture probe and the support capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

The kit optionally also includes instructions for using the kit to capture and optionally detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of target capture probes per subset, configuration of the target capture probes and/or support capture probes, number of nucleic acids of interest and of selected positions on the solid support and subsets of target capture probes, type of support, source of the sample and/or nucleic acids, and/or the like.

Systems

In one aspect, the invention includes systems, e.g., systems used to practice the methods herein and/or comprising the compositions described herein. The system can include, e.g., a fluid and/or microsphere handling element, a fluid and/or microsphere containing element, a laser for exciting a fluorescent label and/or fluorescent microspheres, a detector for detecting light emissions from a chemiluminescent reaction or fluorescent emissions from a fluorescent label and/or fluorescent microspheres, a thermal cycler, and/or a robotic element that moves other components of the system from place to place as needed (e.g., a multiwell plate handling element). For example, in one class of embodiments, a composition of the invention is contained in a flow cytometer, a Luminex 100™ or HTST™ instrument, a microplate reader, a microarray reader, a luminometer, a colorimeter, or like instrument. In one class of embodiments, the system automates capture, isolation, detection, and/or amplification of one or more of the nucleic acids of interest.

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or laser). The computer can also receive data from other components of the system, e.g., from a detector, and can interpret the data, provide it to a user in a human readable format, or use that data to initiate further operations, in accordance with any programming by the user.

Labels

A wide variety of labels are well known in the art and can be adapted to the practice of the present invention. For example, luminescent labels and light-scattering labels (e.g., colloidal gold particles) have been described. See, e.g., Csaki et al. (2002) "Gold nanoparticles as novel label for DNA diagnostics" Expert Rev Mol Diagn 2:187-93.

As another example, a number of fluorescent labels are well known in the art, including but not limited to, hydrophobic fluorophores (e.g., phycoerythrin, rhodamine, Alexa Fluor 488 and fluorescein), green fluorescent protein (GFP) and variants thereof (e.g., cyan fluorescent protein and yellow fluorescent protein), and quantum dots. See e.g., Haughland (2003) Handbook of Fluorescent Probes and Research Products, Ninth Edition or Web Edition, from Molecular Probes, Inc., or The Handbook: A Guide to Fluorescent Probes and Labeling Technologies, Tenth Edition or Web Edition (2006) from Invitrogen (available on the world wide web at probes.invitrogen.com/handbook) for descriptions of fluorophores emitting at various different wavelengths (including tandem conjugates of fluorophores that can facilitate simultaneous excitation and detection of multiple labeled species). For use of quantum dots as labels for biomolecules, see e.g., Dubertret et al. (2002) Science 298:1759; Nature Biotechnology (2003) 21:41-46; and Nature Biotechnology (2003) 21:47-51.

Labels can be introduced to molecules, e.g. polynucleotides, during synthesis or by postsynthetic reactions by techniques established in the art; for example, kits for fluorescently labeling polynucleotides with various fluorophores are available from Molecular Probes, Inc. ((www.) molecularprobes.com), and fluorophore-containing phosphoramidites for use in nucleic acid synthesis are commercially available, as are fluorophore-containing nucleotides (e.g., Cy3 or Cy5 labeled dCTP, dUTP, dTTP, and the like). Similarly, signals from the labels (e.g., absorption by and/or fluorescent emission from a fluorescent label) can be detected by essentially any method known in the art. For example, multicolor detection, detection of FRET, fluorescence polarization, and the like, are well known in the art.

Microspheres

Microspheres are preferred particles in certain embodiments described herein since they are generally stable, are widely available in a range of materials, surface chemistries and uniform sizes, and can be fluorescently dyed. Microspheres can optionally be distinguished from each other by identifying characteristics such as their size (diameter) and/or their fluorescent emission spectra, for example.

Luminex Corporation ((www.) luminexcorp.com), for example, offers 100 sets of uniform diameter polystyrene microspheres. The microspheres of each set are internally labeled with a distinct ratio of two fluorophores. A flow cytometer or other suitable instrument can thus be used to classify each individual microsphere according to its predefined fluorescent emission ratio. Fluorescently-coded microsphere sets are also available from a number of other suppliers, including Radix Biosolutions ((www.) radixbiosolutions.com) and Upstate Biotechnology ((www.) upstatebiotech.com). Alternatively, BD Biosciences ((www.) bd.com) and Bangs Laboratories, Inc. ((www.) bangslabs.com) offer microsphere sets distinguishable by a combination of fluorescence and size. As another example, microspheres can be distinguished on the basis of size alone, but fewer sets of such microspheres can be multiplexed in an assay because aggregates of smaller microspheres can be difficult to distinguish from larger microspheres.

Microspheres with a variety of surface chemistries are commercially available, from the above suppliers and others (e.g., see additional suppliers listed in Kellar and Iannone (2002) "Multiplexed microsphere-based flow cytometric assays" Experimental Hematology 30:1227-1237 and Fitzgerald (2001) "Assays by the score" The Scientist 15[11]:25). For example, microspheres with carboxyl, hydrazide or maleimide groups are available and permit covalent coupling of molecules (e.g., polynucleotide support capture probes with free amine, carboxyl, aldehyde, sulfhydryl or other reactive groups) to the microspheres. As another example, microspheres with surface avidin or streptavidin are available and can bind biotinylated support capture probes; similarly, microspheres coated with biotin are available for binding support capture probes conjugated to avidin or streptavidin. In addition, services that couple a capture reagent of the customer's choice to microspheres are commercially available, e.g., from Radix Biosolutions ((www.) radixbiosolutions.com).

Protocols for using such commercially available microspheres (e.g., methods of covalently coupling polynucleotides to carboxylated microspheres for use as support capture probes, methods of blocking reactive sites on the microsphere surface that are not occupied by the polynucleotides, methods of binding biotinylated polynucleotides to avidin-functionalized microspheres, and the like) are typically supplied with the microspheres and are readily utilized and/or adapted by one of skill. In addition, coupling of reagents to microspheres is well described in the literature. For example, see Yang et al. (2001) "BADGE, Beads Array for the Detection of Gene Expression, a high-throughput diagnostic bioassay" Genome Res. 11:1888-98; Fulton et al. (1997) "Advanced multiplexed analysis with the FlowMetrix™ system" Clinical Chemistry 43:1749-1756; Jones et al. (2002) "Multiplex assay for detection of strain-specific antibodies against the two variable regions of the G protein of respiratory syncytial virus" 9:633-638; Camilla et al. (2001) "Flow cytometric microsphere-based immunoassay: Analysis of secreted cytokines in whole-blood samples from asthmatics" Clinical and Diagnostic Laboratory Immunology 8:776-784; Martins (2002) "Development of internal controls for the Luminex instrument as part of a multiplexed seven-analyte viral respiratory antibody profile" Clinical and Diagnostic Laboratory Immunology 9:41-45; Kellar and Iannone (2002) "Multiplexed microsphere-based flow cytometric assays" Experimental Hematology 30:1227-1237; Oliver et al. (1998) "Multiplexed analysis of human cytokines by use of the FlowMetrix system" Clinical Chemistry 44:2057-2060; Gordon and McDade (1997) "Multiplexed quantification of human IgG, IgA, and IgM with the FlowMetrix™ system" Clinical Chemistry 43:1799-1801; U.S. Pat. No. 5,981,180 entitled "Multiplexed analysis of clinical specimens apparatus and methods" to Chandler et al. (Nov. 9, 1999); U.S. Pat. No. 6,449,562 entitled "Multiplexed analysis of clinical specimens apparatus and methods" to Chandler et al. (Sep. 10, 2002); and references therein.

Methods of analyzing microsphere populations (e.g. methods of identifying microsphere subsets by their size and/or fluorescence characteristics, methods of using size to distinguish microsphere aggregates from single uniformly sized microspheres and eliminate aggregates from the analysis, methods of detecting the presence or absence of a fluorescent label on the microsphere subset, and the like) are also well described in the literature. See, e.g., the above references.

Suitable instruments, software, and the like for analyzing microsphere populations to distinguish subsets of microspheres and to detect the presence or absence of a label (e.g., a fluorescently labeled nucleic acid) on each subset are commercially available. For example, flow cytometers are widely available, e.g., from Becton-Dickinson ((www.) bd.com) and Beckman Coulter ((www.) beckman.com). Luminex 100™ and Luminex HTST™ systems (which use microfluidics to align the microspheres and two lasers to excite the microspheres and the label) are available from Luminex Corporation ((www.) luminexcorp.com); the similar Bio-Plex™ Protein Array System is available from Bio-Rad Laboratories, Inc. ((www.) bio-rad.com). A confocal microplate reader suitable for microsphere analysis, the FMAT™ System 8100, is available from Applied Biosystems ((www.) appliedbiosystems.com).

As another example of particles that can be adapted for use in the present invention, sets of microbeads that include optical barcodes are available from CyVera Corporation ((www.) cyvera.com). The optical barcodes are holographically inscribed digital codes that diffract a laser beam incident on the particles, producing an optical signature unique for each set of microbeads.

Molecular Biological Techniques

In practicing the present invention, many conventional techniques in molecular biology, microbiology, and recombinant DNA technology are optionally used. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., Current Protocols, a joint venture between Greene Publishing Associates, Inc. and John Wiley & Sons, Inc., (supplemented through 2006). Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla.

Making Polynucleotides

Methods of making nucleic acids (e.g., by in vitro amplification, purification from cells, or chemical synthesis), methods for manipulating nucleic acids (e.g., by restriction enzyme digestion, ligation, etc.) and various vectors, cell lines and the like useful in manipulating and making nucleic acids are described in the above references.

In addition, essentially any polynucleotide (including, e.g., labeled or biotinylated polynucleotides) can be custom or standard ordered from any of a variety of commercial sources, such as The Midland Certified Reagent Company ((www.) mcrc.com), The Great American Gene Company ((www.) genco.com), ExpressGen Inc. ((www.) expressgen.com), Qiagen (oligos.qiagen.com) and many others.

A label, biotin, or other moiety can optionally be introduced to a polynucleotide, either during or after synthesis. For example, a biotin phosphoramidite can be incorporated during chemical synthesis of a polynucleotide. Alternatively, any nucleic acid can be biotinylated using techniques known in the art; suitable reagents are commercially available, e.g., from Pierce Biotechnology ((www.) piercenet.com). Similarly, any nucleic acid can be fluorescently labeled, for example, by using commercially available kits such as those from Molecular Probes, Inc. ((www.) molecularprobes.com) or Pierce Biotechnology ((www.) piercenet.com), by incorporating a fluorescently labeled phosphoramidite during chemical synthesis of a polynucleotide, or by incorporating a fluorescently labeled nucleotide during enzymatic synthesis of a polynucleotide.

Arrays

In an array of support capture probes on a solid support (e.g., a membrane, a glass or plastic slide, a silicon or quartz chip, a plate, or other spatially addressable solid support), each support capture probe is typically bound (e.g., electrostatically or covalently bound, directly or via a linker) to the support at a unique selected location. Methods of making, using, and analyzing such arrays (e.g., microarrays) are well known in the art. See, e.g., Baldi et al. (2002) DNA Microarrays and Gene Expression: From Experiments to Data Analysis and Modeling, Cambridge University Press; Beaucage (2001) "Strategies in the preparation of DNA oligonucleotide arrays for diagnostic applications" Curr Med Chem 8:1213-1244; Schena, ed. (2000) Microarray Biochip Technology, pp. 19-38, Eaton Publishing; technical note "Agilent SurePrint Technology: Content centered microarray design enabling speed and flexibility" available on the web at chem.agilent.com/temp/rad01539/00039489.pdf; and references therein. Arrays of pre-synthesized polynucleotides can be formed (e.g., printed), for example, using commercially available instruments such as a GMS 417 Arrayer (Affymetrix, Santa Clara, Calif.). Alternatively, the polynucleotides can be synthesized at the selected positions on the solid support; see, e.g., U.S. Pat. Nos. 6,852,490 and 6,306,643, each to Gentanlen and Chee entitled "Methods of using an array of pooled probes in genetic analysis."

Suitable solid supports are commercially readily available. For example, a variety of membranes (e.g., nylon, PVDF, and nitrocellulose membranes) are commercially available, e.g., from Sigma-Aldrich, Inc. ((www.) sigmaaldrich.com). As another example, surface-modified and pre-coated slides with a variety of surface chemistries are commercially available, e.g., from TeleChem International ((www.) arrayit-.com), Corning, Inc. (Corning, N.Y.), or Greiner Bio-One, Inc. ((www.) greinerbiooneinc.com). For example, silanated and silyated slides with free amino and aldehyde groups, respectively, are available and permit covalent coupling of molecules (e.g., polynucleotides with free aldehyde, amine, or other reactive groups) to the slides. As another example, slides with surface streptavidin are available and can bind biotinylated support capture probes. In addition, services that produce arrays of polynucleotides of the customer's choice are commercially available, e.g., from TeleChem International ((www.) arrayit.com) and Agilent Technologies (Palo Alto, Calif.).

Suitable instruments, software, and the like for analyzing arrays to distinguish selected positions on the solid support and to detect the presence or absence of a label (e.g., a fluorescently labeled nucleic acid) at each position are commercially available. For example, microarray readers are available, e.g., from Agilent Technologies (Palo Alto, Calif.), Affymetrix (Santa Clara, Calif.), and Zeptosens (Switzerland).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Multiplex Capture of Nucleic Acids

The following sets forth a series of experiments that demonstrate design of support capture probes and corresponding target capture probes for multiplex capture of nucleic acids. Unique sequences of 15 bases were chosen as support capture probes. The support capture probes were designed to have minimal potential for secondary structure formation or cross-hybridization. They were also screened against homology with sequences of human, mouse or rat genes. Oligonucleotide support capture probes were synthesized with 5'-amino linker (BioSearch) and covalently linked to carboxylated fluorescent-encoded microsphere beads (Luminex Corporation) following the recommended conjugation procedure from Luminex. Each support capture probe was coupled to a different, fluorescently-labeled subset of the beads.

Figure 4:
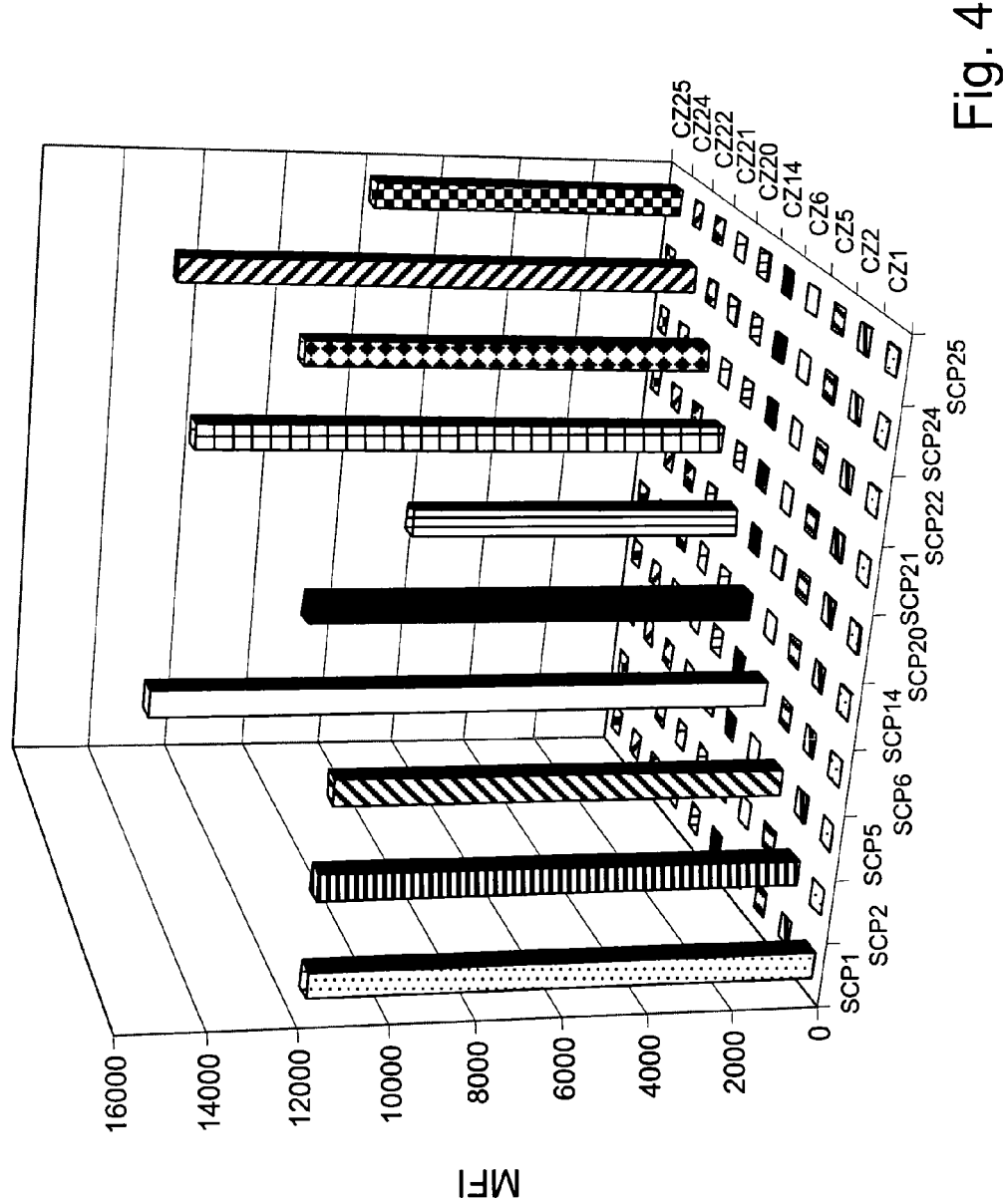
FIG. 4 depicts a graph illustrating evaluation of ten support capture probes for cross hybridization with ten biotin-labeled probes, one complementary to each of the support capture probes. Biotin-labeled probes are named on the x-axis, beads with associated support capture probes are represented by number on the y-axis, and median fluorescent intensity is plotted on the z-axis.

Each bead subset was examined for specific hybridization to a biotinylated oligonucleotide complementary to the support capture probe associated with that subset of beads, as well as for its non-specific hybridization to the other biotinylated oligonucleotides. The biotinylated oligonucleotides were detected with streptavidin-conjugated R-phycoerythrin. As illustrated in FIG. 4, when 16.5 fmol of an individual biotin-labeled complementary probe (represented by name in x-axis) is added into a mixture of ten support capture probe-conjugated beads, only the corresponding bead (represented by the SCP number in y-axis) gives strong fluorescent signal (z-axis, background subtracted median fluorescent intensity from 100 counted beads); the other beads show minimal fluorescent signal above background. The assay signals of all possible non-specific hybridizations were less than 0.1% of those observed for the perfectly matched pair, indicating a very high degree of hybridization specificity. Thus the set of support capture probes was shown to be highly specific and can be used for multiplex capture of target nucleic acids.

Ten subsets of target capture probes were designed. Each target capture probe is complementary to one of the ten support capture probes and to one of ten target nucleic acids. The subsets of target capture probes can be used in conjunction with the support capture probe-conjugated beads (or, e.g., with a support capture probe-conjugated spatially addressable solid support) to specifically capture, e.g., mRNAs or the like produced from the genes listed in Table 1. Sequences of the support capture probes and target capture probes are presented in Table 2.

For example, one or more of the target nucleic acids is optionally captured by hybridization to the corresponding subset of target capture probes, which is in turn hybridized to the corresponding support-bound support capture probe, under any of a variety of suitable hybridization conditions. As one example, the target nucleic acids are optionally captured by hybridization in a solution that includes 127 mM LiCl, 5% lithium lauroyl sulfate, 9 mM EDTA, 50 mM HEPES (pH 7.5), 0.05% hespan (DuPont Pharmaceuticals), 0.05% Pro-Clin 300 (Supelco), and 0.2% casein (Research Organics, Hammarsten quality), along with the target nucleic acid(s), support-bound support capture probes, and target capture probes (e.g., about 16.5 fmol of each target capture probe in a 100 μl assay volume), at a hybridization temperature of 53° C. for about 16 hours. The support is optionally washed, e.g., with a wash buffer that includes 0.1×SSC and 0.3% lithium lauryl sulfate, to remove materials not captured on the support.

About 2000 beads per subset are typically used for capture and optional detection of the listed mRNAs, e.g., from cell lysates. It will be evident, however, that the number of particles (e.g., beads) per subset is optionally optimized for the desired application. For example, the number of particles per subset can be increased, e.g., in embodiments in which capture of substantially all of a particular nucleic acid of interest present in a sample is desired (including, e.g., embodiments in which the nucleic acid is present at very low concentration), or decreased, e.g., to increase sensitivity of detection for a nucleic acid of interest present at very low concentration in the sample by maximizing the number of molecules of that nucleic acid captured per bead in embodiments in which fluorescently labeled nucleic acids are being detected. By increasing the number of particles used, even less than 0.001 amol or 10-50 copies of a target nucleic acid can optionally be captured (and subsequently amplified, detected, or the like, if desired).

TABLE 1

Target names and reference sequence accession numbers for the target nucleic acids.

| Target Symbol | Accession Number |
|---|---|
| IL2 | NM_000586 |
| TNF | NM_000594 |
| VEGF | NM_003376 |
| IL10 | NM_000572 |

TABLE 1-continued

Target names and reference sequence accession numbers for the target nucleic acids.

| Target Symbol | Accession Number |
|---|---|
| IL6 | NM_000600 |
| IL1B | NM_000576 |
| IFNG | NM_000619 |
| IL8 | NM_000584 |
| CSF2 | NM_000758 |
| GAPD | NM_002046 |

TABLE 2

Support capture probe (SCP) and target capture probe (TCP) sequences for multiplex capture of the targets listed in Table 1.

| Gene Name | | Sequence | SEQ ID NO |
|---|---|---|---|
| CSF2 | TCP | agcagcaggctctgcagcTTTTTttgtgcagtgttata | 1 |
| CSF2 | TCP | gcgggtgcagagatgctgTTTTTttgtgcagtgttata | 2 |
| CSF2 | TCP | tacagctccaggcgggtcTTTTTttgtgcagtgttata | 3 |
| CSF2 | TCP | tgagcttggtgaggctgccTTTTTttgtgcagtgttata | 4 |
| CSF2 | TCP | tgcttgtagtggctggccaTTTTTttgtgcagtgttata | 5 |
| CSF2 | SCP (CP24) | TTTTTTTTTATAACACTGCACAA | 6 |
| GAPD | TCP | tgacggtgccatggaatttTTTTTaaaactatacgtgct | 7 |
| GAPD | TCP | agcttcccgttctcagcctTTTTTaaaactatacgtgct | 8 |
| GAPD | TCP | tctcgctcctggaagatggtTTTTTaaaactatacgtgct | 9 |
| GAPD | TCP | gcaaatgagccccagccTTTTTaaaactatacgtgct | 10 |
| GAPD | TCP | ccttttggctcccccctTTTTTaaaactatacgtgct | 11 |
| GAPD | TCP | catggatgaccttggccagTTTTTaaaactatacgtgct | 12 |
| GAPD | TCP | gctcagggatgaccttgccTTTTTaaaactatacgtgct | 13 |
| GAPD | SCP (CP25) | TTTTTTTTAGCACGTATAGTTTT | 14 |
| IFNG | TCP | cactctcctctttccaattcttcaTTTTTTTtcacacacattaac | 15 |
| IFNG | TCP | ttggctctgcattatttttctgtTTTTTttcacacacattaac | 16 |
| IFNG | TCP | tctcgtttcttttgttgctattgTTTTTttcacacacattaac | 17 |
| IFNG | TCP | atgagttcatgtattgctttgcgtTTTTTttcacacacattaac | 18 |
| IFNG | TCP | ttccctgttttagctgctggTTTTTttcacacacattaac | 19 |

TABLE 2-continued

Support capture probe (SCP) and target capture probe (TCP) sequences for multiplex capture of the targets listed in Table 1.

| Gene Name | | | SEQ ID NO |
|---|---|---|---|
| IFNG | TCP | atattccccatataaataatgttaaatatttTT TTTtttcacacacattaac | 20 |
| IFNG | SCP (CP20) | TTTTTTTTGTTAATGTGTGTGAA | 21 |
| IL1 | TCP | agtgggtgcagctgttctcaTTTTTccgtgct tttctaat | 22 |
| IL1 | TCP | ctcggagatctcgaagcatgtTTTTTccgtgc ttttctaat | 23 |
| IL1 | TCP | gctgatccttcatttgaaagaaaTTTTTccgt gcttttctaat | 24 |
| IL1 | TCP | ctgggtcttggttctcagcttTTTTTccgtgc ttttctaat | 25 |
| IL1 | TCP | gcctcagcctgagggtcttTTTTTccgtgctt ttctaat | 26 |
| IL1 | TCP | ccgattttggagacctctaatttaTTTTTccg tgcttttctaat | 27 |
| IL1 | SCP (CP5) | TTTTTTTTATTAGAAAAGCACGG | 28 |
| IL1B | TCP | gcagaggtccaggtcctggTTTTTaacgtgta ttccatt | 29 |
| IL1B | TCP | tgaagcccttgctgtagtggtTTTTTaacgtg tattccatt | 30 |
| IL1B | TCP | cctggaaggtctgtgggcaTTTTTaacgtgta ttccatt | 31 |
| IL1B | TCP | aaagaaggtgctcaggtcattctTTTTTaacg tgtattccatt | 32 |
| IL1B | TCP | ggagagctttcagttcatatggaTTTTTaacg tgtattccatt | 33 |
| IL1B | TCP | ccatatcctgtccctggaggtTTTTTaacgtg tattccatt | 34 |
| IL1B | TCP | attcttttccttgaggcccaTTTTTaacgtgt attccatt | 35 |
| IL1B | SCP (CP14) | TTTTTTTTAATGGAATACACGTT | 36 |
| IL2 | TCP | tgagtttgggattcttgtaattattaaTTTTT gaagttaccgttttc | 37 |
| IL2 | TCP | tggccttcttgggcatgtaTTTTTgaagttac cgttttc | 38 |
| IL2 | TCP | ctccagaggtttgagttcttcttcTTTTTgaa gttaccgttttc | 39 |
| IL2 | TCP | tcagatcccttagttccagaactTTTTTgaa gttaccgttttc | 40 |
| IL2 | TCP | aataaatagaaggcctgatatgttttaTTTTT gaagttaccgttttc | 41 |
| IL2 | SCP (CP1) | TTTTTTTTGAAAACGGTAACTTC | 42 |
| IL6 | TCP | gagcttctctttcgttcccgTTTTTggggaac atagaaaa | 43 |
| IL6 | TCP | tgtggagaaggagttcatagctgTTTTTgggg aacatagaaaa | 44 |
| IL6 | TCP | agccccagggagaaggcTTTTTggggaacata gaaaa | 45 |
| IL6 | TCP | tgtctcctttctcagggctgaTTTTTggggaa catagaaaa | 46 |
| IL6 | TCP | cctcattgaatccagattggaaTTTTTgggga acatagaaaa | 47 |
| IL6 | TCP | gaagagccctcaggctggaTTTTTggggaaca tagaaaa | 48 |
| IL6 | SCP (CP6) | TTTTTTTTTTTTCTATGTTCCCC | 49 |
| IL8 | TCP | tgcacccagttttccttggTTTTTttcaaatg ttagcct | 50 |
| IL8 | TCP | ttttatgaattctcagccctcttTTTTTttca atgttagcct | 51 |
| IL8 | TCP | cggatattctcttggcccttTTTTTttcaaat gttagcct | 52 |
| IL8 | TCP | tgtggatcctggctagcagaTTTTTttcaaat gttagcct | 53 |
| IL8 | TCP | acccaattgtttgtttgtttaatcTTTTTttc aaatgttagcct | 54 |
| IL8 | SCP (CP22) | TTTTTTTTAGGCTAACATTTGAA | 55 |
| TNF | TCP | cgagaagatgatctgactgcctgTTTTTctga gtcaaagcatt | 56 |
| TNF | TCP | gctgcccctcagcttgagTTTTTctgagtcaa agcatt | 57 |
| TNF | TCP | gtctggtaggagacggcgatTTTTTctgagtc aaagcatt | 58 |
| TNF | TCP | tcccagatagatgggctcatacTTTTTctgag tcaaagcatt | 59 |
| TNF | TCP | tcgggccgattgatctcaTTTTTctgagtcaa agcatt | 60 |
| TNF | TCP | cccccaattctcttttgagcTTTTTctgagt caaagcatt | 61 |
| TNF | SCP (CP2) | TTTTTTTTAATGCTTTGACTCAG | 62 |
| VEGF | TCP | aaggctccaatgcacccaTTTTTaggttttgg attcat | 63 |
| VEGF | TCP | ctgccatgggtgcagccTTTTTaggttttgga ttcat | 64 |
| VEGF | TCP | tggtgaggtttgatccgcaTTTTTaggttttg gattcat | 65 |
| VEGF | TCP | atctctcctatgtgctggcctTTTTTaggtt ttggattcat | 66 |
| VEGF | TCP | atctttctttggtctgcattcacTTTTTagg ttttggattcat | 67 |

TABLE 2-continued

Support capture probe (SCP) and target capture probe (TCP) sequences for multiplex capture of the targets listed in Table 1.

| Gene Name | | SEQ ID NO |
|---|---|---|
| VEGF TCP | ccctttccctttcctcgaaTTTTTaggtttt ggattcat | 68 |
| VEGF TCP | ccaggacttataccgggatttcTTTTTaggt tttggattcat | 69 |
| VEGF SCP (CP21) | TTTTTTTTATGAATCCAAAACCT | 70 |

While the foregoing invention has been described in some detail for purposes of clarity and understanding, it will be clear to one skilled in the art from a reading of this disclosure that various changes in form and detail can be made without departing from the true scope of the invention. For example, all the techniques and compositions described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of capturing ten or more different nucleic acids of interest, the method comprising:

providing a sample comprising the ten or more different nucleic acids of interest;

providing a pooled population of particles, the population comprising ten or more subsets of particles, the particles in each subset having associated therewith a different support capture probe, which support capture probe comprises only naturally occurring bases A, C, G, T, and/or U;

providing ten or more subsets of at least two different target capture probes, which target capture probes comprise only naturally occurring bases A, C, G, T, and/or U, wherein a different subset of target capture probes is provided for each different nucleic acid of interest, wherein the at least two different target capture probes in each subset are capable of hybridizing to nonoverlapping polynucleotide sequences in the corresponding nucleic acid of interest, and wherein the target capture probes in each subset are capable of hybridizing to a different one of the support capture probes and thereby associating each subset of target capture probes with a different selected subset of the particles;

contacting the sample, the pooled population of particles, and the subsets of target capture probes; and, for each of the nucleic acids of interest, hybridizing the nucleic acid to its corresponding subset of at least two different target capture probes and hybridizing the subset of target capture probes to its corresponding support capture probe, thereby capturing the nucleic acid on the subset of particles with which the target capture probes are associated, wherein the hybridizing the subset of at least two different target capture probes to the corresponding support capture probe is performed in the presence of the nucleic acid and at a hybridization temperature which is greater than a melting temperature $T_m$ of a complex between each individual target capture probe and its corresponding support capture probe.

2. The method of claim 1, wherein a plurality of the particles in each subset are distinguishable from a plurality of the particles in every other subset.

3. The method of claim 1, wherein the ten or more different nucleic acids of interest comprise 20 or more different nucleic acids of interest, wherein the ten or more subsets of particles comprise 20 or more subsets of particles, and wherein the ten or more subsets of at least two different target capture probes comprise 20 or more subsets of at least two different target capture probes.

4. The method of claim 1, wherein the particles are microspheres.

5. The method of claim 4, wherein the microspheres of each subset are distinguishable from those of the other subsets on the basis of their fluorescent emission spectrum, their diameter, or a combination thereof.

6. The method of claim 1, wherein providing ten or more subsets of at least two different target capture probes comprises providing ten or more subsets of at least three different target capture probes.

7. The method of claim 6, wherein providing ten or more subsets of at least three different target capture probes comprises providing ten or more subsets of at least five different target capture probes.

8. The method of claim 1, wherein providing ten or more subsets of at least two different target capture probes comprises providing ten or more subsets of at most ten different target capture probes.

9. The method of claim 1, wherein each target capture probe comprises a polynucleotide sequence U-1 that is complementary to a polynucleotide sequence U-2 in its corresponding support capture probe, and wherein U-1 and U-2 are 20 nucleotides or less in length.

10. The method of claim 9, wherein U-1 and U-2 are between 9 and 17 nucleotides in length.

11. The method of claim 10, wherein U-1 and U-2 are between 12 and 15 nucleotides in length.

12. The method of claim 1, wherein the hybridization temperature is about 5° C. or more greater than the $T_m$.

13. The method of claim 12, wherein the hybridization temperature is about 7° C. or more, about 10° C. or more, about 12° C. or more, about 15° C. or more, about 17° C. or more, or about 20° C. or more greater than the $T_m$.

14. The method of claim 1, wherein contacting the sample, the pooled population of particles, and the subsets of target capture probes comprises combining the sample with the subsets of target capture probes to form a mixture, and then combining the mixture with the pooled population of particles.

15. The method of claim 1, wherein a plurality of the particles in each subset are distinguishable from a plurality of the particles in every other subset, the method comprising determining which subsets of particles have a nucleic acid of interest captured on the particles, thereby indicating which of the nucleic acids of interest were present in the sample.

16. The method of claim 15, wherein each of the nucleic acids of interest comprises a label, and wherein determining which subsets of particles have a nucleic acid of interest captured on the particles comprises detecting a signal from the label.

17. The method of claim 16, wherein detecting the signal from the label comprises measuring an intensity of the signal from the label, the method comprising correlating the intensity of the signal with a quantity of the corresponding nucleic acid of interest present.

18. The method of claim 16, wherein the label is a fluorescent label.

19. The method of claim 15, wherein determining which subsets of particles have a nucleic acid of interest captured on the particles comprises amplifying any nucleic acid of interest captured on the particles.

20. The method of claim 1, comprising isolating one or more subsets of particles, whereby any nucleic acid of interest captured on the particles is isolated.

21. The method of claim 1, comprising separating materials not captured on the particles from the particles.

22. The method of claim 1, wherein the sample was derived from one or more of: an animal, a human, a plant, a cultured cell, a virus, a bacterium, a pathogen, or a microorganism.

23. The method of claim 1, wherein the sample comprises one or more of: a cell lysate, an intercellular fluid, a bodily fluid, or a conditioned culture medium.

24. The method of claim 1, wherein the sample is derived from one or more of: a tissue, a biopsy, or a tumor.

25. The method of claim 1, wherein the nucleic acids of interest are derived from one or more of: an animal, a human, a plant, a cultured cell, a microorganism, a virus, a bacterium, or a pathogen.

26. The method of claim 1, wherein the ten or more different nucleic acids of interest comprise ten or more different mRNAs.

27. The method of claim 1, wherein at least one of the nucleic acids of interest is present in the sample in a non-zero amount of 200 amol or less, 150 amol or less, 100 amol or less, 50 amol or less, 10 amol or less, 1 amol or less, or 0.1 amol or less.

28. The method of claim 1, wherein the sample comprises a first nucleic acid of interest, and wherein at least 30%, at least 50%, at least 80%, at least 90%, or at least 95% of a total amount of the first nucleic acid present in the sample is captured on a first subset of particles.

29. The method of claim 1, wherein the sample comprises a first nucleic acid of interest and a different second nucleic acid, the second nucleic acid having a polynucleotide sequence which is 95% or more identical to that of the first nucleic acid, wherein the first nucleic acid is captured on a first subset of particles, and wherein the second nucleic acid comprises 1% or less of a total amount of nucleic acid captured on the first subset of particles.

30. The method of claim 1, wherein the sample comprises a first nucleic acid of interest and a different second nucleic acid, the first nucleic acid being a first splice variant and the second nucleic acid being a second splice variant, wherein a first subset of n target capture probes is capable of hybridizing to the first splice variant, of which at most n−1 target capture probes are capable of hybridizing to the second splice variant.

31. The method of claim 30, wherein hybridization of the n target capture probes to the first splice variant captures the first splice variant on a first subset of particles while hybridization of the at most n−1 target capture probes to the second splice variant does not capture the second splice variant on the first subset of particles.

32. A method of capturing ten or more different nucleic acids of interest, the method comprising:
providing a sample comprising the ten or more different nucleic acids of interest;
providing a solid support comprising ten or more different support capture probes, which support capture probes comprise only naturally occurring bases A, C, G, T, and/or U, wherein each different support capture probe is provided at a different selected position on the solid support;
providing ten or more subsets of at least two different target capture probes, which target capture probes comprise only naturally occurring bases A, C, G, T, and/or U, wherein a different subset of target capture probes is provided for each different nucleic acid of interest, wherein the at least two different target capture probes in each subset are capable of hybridizing to nonoverlapping polynucleotide sequences in the corresponding nucleic acid of interest, and wherein the target capture probes in each subset are capable of hybridizing to a different one of the support capture probes and thereby associating each subset of target capture probes with a different selected position on the solid support;
contacting the sample, the solid support, and the subsets of target capture probes; and,
for each of the nucleic acids of interest, hybridizing the nucleic acid to its corresponding subset of at least two different target capture probes and hybridizing the subset of target capture probes to its corresponding support capture probe, thereby capturing the nucleic acid on the solid support at the selected position with which the target capture probes are associated,
wherein the hybridizing the subset of at least two different target capture probes to the corresponding support capture probe is performed in the presence of the nucleic acid and at a hybridization temperature which is greater than a melting temperature $T_m$ of a complex between each individual target capture probe and its corresponding support capture probe.

33. The method of claim 32, wherein the hybridization temperature is about 7° C. or more, about 10° C. or more, about 12° C. or more, about 15° C. or more, about 17° C. or more, or about 20° C. or more greater than the $T_m$.

34. The method of claim 32, wherein the ten or more different nucleic acids of interest comprise 20 or more, 30 or more, 40 or more, 50 or more, 100 or more, $10^3$ or more, or $10^4$ or more different nucleic acids of interest.

35. The method of claim 32, wherein providing ten or more subsets of at least two different target capture probes comprises providing ten or more subsets of at least three different target capture probes.

36. The method of claim 35, wherein providing ten or more subsets of at least three different target capture probes comprises providing ten or more subsets of at least five different target capture probes.

37. The method of claim 32, wherein providing ten or more subsets of at least two different target capture probes comprises providing ten or more subsets of at most ten different target capture probes.

38. The method of claim 32, wherein each target capture probe comprises a polynucleotide sequence U-1 that is complementary to a polynucleotide sequence U-2 in its corresponding support capture probe, and wherein U-1 and U-2 are 20 nucleotides or less in length.

39. The method of claim 38, wherein U-1 and U-2 are between 9 and 17 nucleotides in length.

40. The method of claim 39, wherein U-1 and U-2 are between 12 and 15 nucleotides in length.

* * * * *